United States Patent
Xiao et al.

(10) Patent No.: US 11,407,783 B2
(45) Date of Patent: Aug. 9, 2022

(54) TRIPTOLIDE DERIVATIVE AND PREPARATION METHOD THEREFOR AND USE THEREOF

(71) Applicants: Cinkate Pharmaceutical Intermediates Co., Ltd., Shanghai (CN); Cinkate Pharm Tech (Shanghai) Co., Ltd., Shanghai (CN)

(72) Inventors: Fei Xiao, Shanghai (CN); Bo Qiu, Shanghai (CN); Peng Zhang, Shanghai (CN)

(73) Assignees: CINKATE PHARMACEUTICAL INTERMEDIATES CO., LTD., Shanghai (CN); CINKATE PHARM TECH (SHANGHAI) CO., LTD., Shanghai (CN)

(*) Notice: Subject to any disclaimer, the term of this patent is extended or adjusted under 35 U.S.C. 154(b) by 0 days.

(21) Appl. No.: 16/757,799

(22) PCT Filed: Apr. 18, 2018

(86) PCT No.: PCT/CN2018/083525
§ 371 (c)(1),
(2) Date: Apr. 21, 2020

(87) PCT Pub. No.: WO2019/192031
PCT Pub. Date: Oct. 10, 2019

(65) Prior Publication Data
US 2021/0238221 A1    Aug. 5, 2021

(30) Foreign Application Priority Data
Apr. 2, 2018 (CN) .......................... 201810283385.5

(51) Int. Cl.
| | | |
|---|---|---|
| *C07J 73/00* | (2006.01) | |
| *A61K 9/00* | (2006.01) | |
| *A61P 35/00* | (2006.01) | |
| *A61P 37/06* | (2006.01) | |

(52) U.S. Cl.
CPC ........... *C07J 73/003* (2013.01); *A61K 9/0019* (2013.01); *A61P 35/00* (2018.01); *A61P 37/06* (2018.01)

(58) Field of Classification Search
CPC ...... C07J 73/003; A61K 9/0019; A61P 35/00; A61P 37/06
See application file for complete search history.

(56) References Cited

FOREIGN PATENT DOCUMENTS

| CN | 1925852 A | 3/2007 |
|----|-----------|--------|
| CN | 107663225 A | 2/2018 |
| WO | 2005084365 A2 | 9/2005 |

OTHER PUBLICATIONS

Int'l Search Report dated Jan. 14, 2019 in Int'l Application No. PCT/CN2018/083525.
Xu et al., "Design, Synthesis and Structure-Activity Relationships Studies on the D Ring of the Natural Product Triptolide," ChemMedChem, vol. 9, pp. 290-295 (2014).

*Primary Examiner* — Brenda L Coleman
(74) *Attorney, Agent, or Firm* — Panitch Schwarze Belisario & Nadel LLP

(57) ABSTRACT

A triptolide derivative, a preparation method therefor, and a method for use thereof are described. The triptolide derivative has the structure as shown in general formula I, and the definition of each substituent is as described in the description and claims. The triptolide derivative has improved immunosuppressive activity and anti-tumor activity, low toxicity and high safety, thus having good development and application prospects.

11 Claims, 1 Drawing Sheet

TRIPTOLIDE DERIVATIVE AND PREPARATION METHOD THEREFOR AND USE THEREOF

CROSS-REFERENCE TO RELATED APPLICATION

This application is a Section 371 of International Application No. PCT/CN2018/083525, filed Apr. 18, 2018, which was published in the Chinese language on Oct. 10, 2019 under International Publication No. WO 2019/192031 A1, which claims priority under 35 U.S.C. § 119(b) to Chinese Application No. 201810283385.5, filed. Apr. 2, 2018, the disclosures of which are incorporated herein by reference in their entirety.

TECHNICAL FIELD

The invention relates to the field of medicinal chemistry, and in particular to a triptolide derivative having antitumor activity and immunosuppressive activity, and a preparation method therefor and use thereof.

BACKGROUND TECHNIQUE

Natural products have always been the main source of new anti-tumor drugs. However, these compounds often have poor pharmacokinetic properties, and only a few pure natural products have been developed into anti-tumor drugs in clinic.

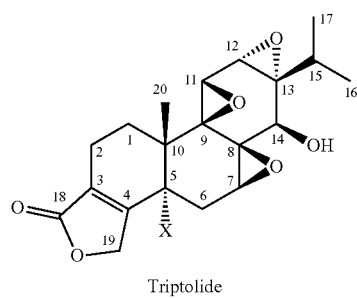

Triptolide

The Chinese herbal plant *Tripterygium wilfordii* (TW) is a common research object for antitumor drug. Currently, the compound triptolide extracted from TW is an important active ingredient of *Tripterygium wilfordii* and it has been found in studies that it has anti-inflammatory, anti-tumor and immunosuppressive activities. At the same time, it has been found in the studies that triptolide has greater toxicity and various adverse reactions, which seriously affect the development and utilization of triptolide. In vivo experiments have shown that the safety range of triptolide is very narrow. Two or four times of the effective dose of triptolide can cause animal death, and it is even reported in some studies that the effective dose is very close to the lethal dose. In toxicological studies, it has been found that the adverse reactions of triptolide involve a variety of tissues and organs, including the gastrointestinal tract, kidney, heart, liver, hematopoietic system and reproductive system. Therefore, it is an important research direction in scientific research to carry out structural modification of triptolide to obtain a highly effective and low-toxic triptolide derivative, which can exert anti-tumor and other biological activities while avoiding toxicity.

Based on literature survey, it is found that the structural modifications of triptolide are focused on the C14 hydroxyl, C7/C8 epoxy, C12/C13 epoxy, and unsaturated lactone ring. Among them, the structural modification of the unsaturated lactone ring mainly converts the lactone ring into a furan ring or into a lactam, or opens the lactone ring to increase the water solubility. However, these two strategies will lead to a reduction or even disappearance of activity in the derivatives.

SUMMARY OF THE INVENTION

The purpose of the present invention is to provide a triptolide derivative with novel structure, and a preparation method therefor and use thereof.

In the first aspect of the present invention, it provides a compound represented by formula I, or a pharmaceutically acceptable salt thereof, or an enantiomer, a diastereomer, a tautomer, a solvate, a polymorph or a prodrug thereof,

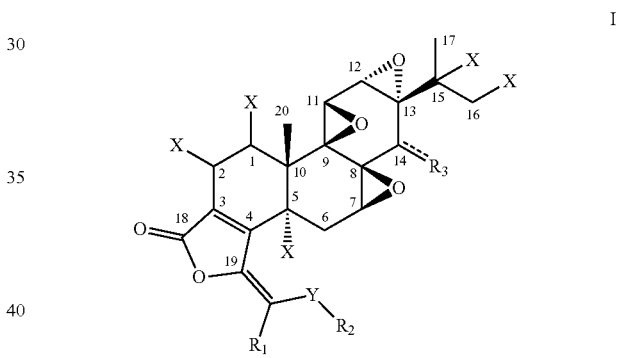

wherein, $R_1$ is a substituted or unsubstituted group selected from the group consisting of: C1-C6 alkyl, C3-C8 cycloalkyl, C2-C6 alkenyl, C3-C8 cycloalkenyl, C2-C6 alkynyl, C6-C10 aryl. C7-C15 arylalkyl and 4-8 membered heteroaryl;

Y is O, NH or S;

$R_2$ is a substituted or unsubstituted group selected from the group consisting of: C1-C6 alkyl, C3-C8 cycloalkyl, C2-C6 alkenyl, C3-C8 cycloalkenyl, C2-C6 alkynyl, C6-C10 aryl, C7-C15 arylalkyl, 4-8 membered heteroaryl and —C(=O)$R_4$, wherein $R_4$ is a substituted or unsubstituted group selected from the group consisting of: C1-C6 alkyl, C3-C8 cycloalkyl, C2-C6 alkenyl, C3-C8 cycloalkenyl, C2-C6 alkynyl, C6-C10 aryl, C7-C15 arylalkyl and 4-8 membered heteroaryl;

═╌═ represents a double bond or a single bond, when it is a double bond, $R_3$ is O; when it is a single bond. $R_3$ is $OR_5$, F or SH, and $R_5$ is H, Boc, TBS, TES, $CH_2SCH_3$, $CH_2OCH_3$, —OP(=O)(OH)$_2$, —OP(=O)(OBn)$_2$, —CH$_2$OP(=O)(OH)$_2$, —CH$_2$OP(=O)(OBn)$_2$, —COOH, monosaccharide, folic acid and folic acid analog or monoclonal antibody;

each X is independently H, OH or halogen;

each of the above term "substituted" independently means that one or more hydrogen atoms on the group are substituted with a substituent selected from the group consisting of: halogen, —OH, NH$_2$, CN, COOH, —OP(=O)(OH)$_2$, unsubstituted or halogenated C1-C8 alkyl, unsubstituted or halogenated C3-C8 cycloalkyl, unsubstituted or halogenated C1-C8 alkoxy, unsubstituted or halogenated C2-C6 alkenyl, unsubstituted or halogenated C2-C6 alkynyl, unsubstituted or halogenated C2-C6 acyl, unsubstituted or halogenated C2-C6 amido, unsubstituted or halogenated 5-8 membered aryl, unsubstituted or halogenated 5-8 membered heteroaryl, unsubstituted or halogenated 4-8 membered saturated heterocycle or carbocycle; wherein each of the above heteroaryl groups independently contains 1-3 heteroatoms selected from the group consisting of N, O and S.

In the present application, Boc is tert-butoxycarbonyl, TBS is tert-butyldimethylsilyl, and TES is triethylsilyl.

In another preferred embodiment, $R_3$ is OH, OBoc, OCH$_2$OP(=O)(OH)$_2$, —OCH$_2$OP(=O)(OBn)$_2$, OTBS, OTES, OCH$_2$SCH$_3$, or OCH$_2$OCH$_3$. In another preferred embodiment, $R_3$ is OH. In another preferred embodiment, $R_3$ is β-OH. In another preferred embodiment. $R_3$ is OBoc, OCH$_2$OP(=O)(OH) or —OCH$_2$OP(=O)(OBn)$_2$.

In another preferred embodiment, at most one X is OH.

In another preferred embodiment, the configuration of the 14-position carbon is an α-configuration or a β-configuration.

In another preferred embodiment, each X is H.

In another preferred embodiment, Y is O.

In another preferred embodiment, $R_1$ is a substituted or unsubstituted following group: C1-C4 alkyl, C3-C6 cycloalkyl, C6-C10 aryl or 4-8 membered heteroaryl, wherein the term "substituted" means one or more hydrogen atoms on the group are substituted with a substituent selected from the group consisting of halogen, —OH, unsubstituted or halogenated C1-C4 alkyl, and unsubstituted or halogenated C1-C3 alkoxy.

In another preferred embodiment, $R_1$ is cyclohexyl, n-propyl, n-butyl, phenyl, 2-furyl, p-methylphenyl, p-methoxyphenyl, or p-trifluoromethylphenyl.

In another preferred embodiment, $R_2$ is a substituted or unsubstituted group selected from the group consisting of: C1-C4 alkyl, C7-C10 arylalkyl, 4-6 membered heteroaryl or —C(=O)R$_4$, wherein $R_4$ is a substituted or unsubstituted group selected from the group consisting of: C1-C4 alkyl, C3-C6 cycloalkyl, C6-C10 aryl, C7-C15 arylalkyl or 4-8 membered heteroaryl, wherein the term "substituted" means one or more hydrogen atoms on the group are substituted with a substituent selected from the group consisting of halogen, —OH, unsubstituted or halogenated C1-C4 alkyl, and unsubstituted or halogenated C1-C3 alkoxy.

In another preferred embodiment, $R_2$ is C1-C4 alkyl, C7-C10 arylalkyl or (CO)R$_4$. In another preferred embodiment, $R_2$ is methyl, ethyl, propyl or butyl. In another preferred embodiment, $R_4$ is a substituted or unsubstituted following group: C1-C4 alkyl, C3-C6 cycloalkyl, C6-C10 aryl and 4-8 membered heteroaryl.

In another preferred embodiment, $R_4$ is cyclohexyl, n-butyl, n-propyl, phenyl, 2-furyl, p-methylphenyl, p-trifluoromethylphenyl, or p-methoxyphenyl.

In another preferred embodiment, $R_1$ and $R_2$ are the same or different.

In another preferred embodiment, $R_1$ and $R_4$ are the same or different.

In another preferred embodiment, the compound is:

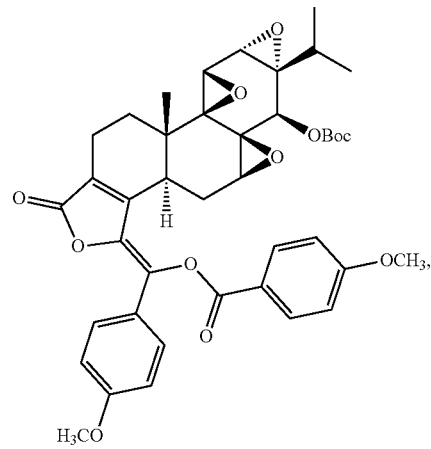

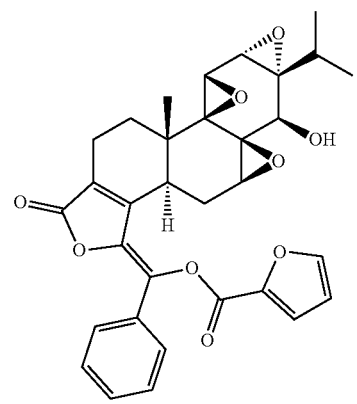

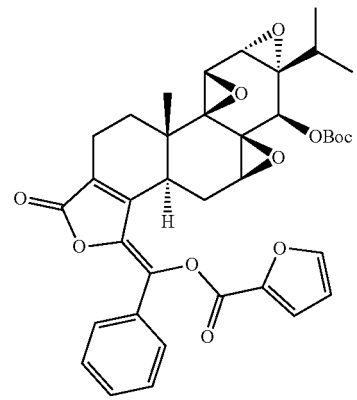

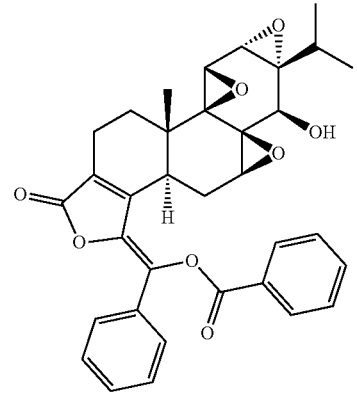

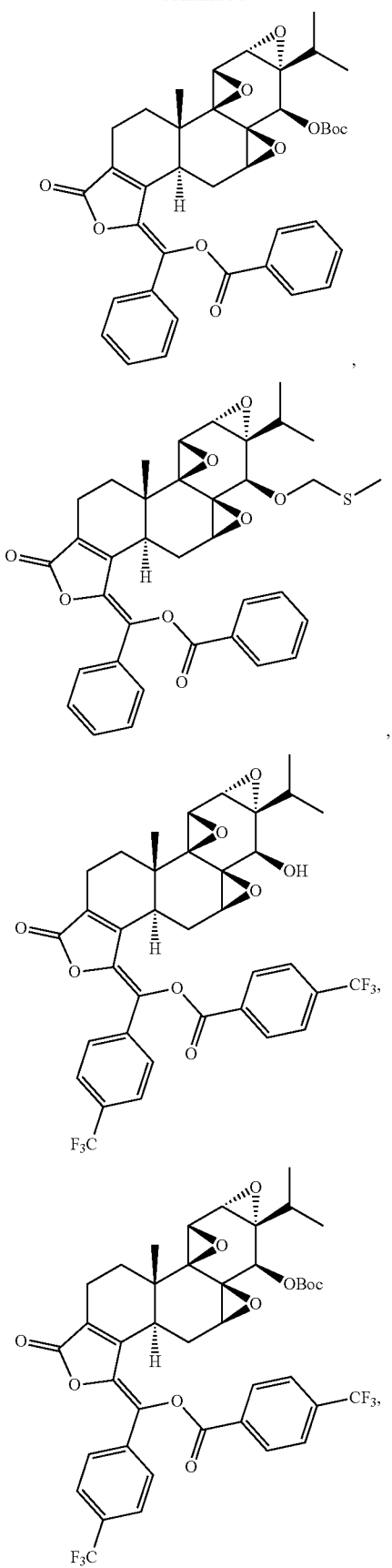
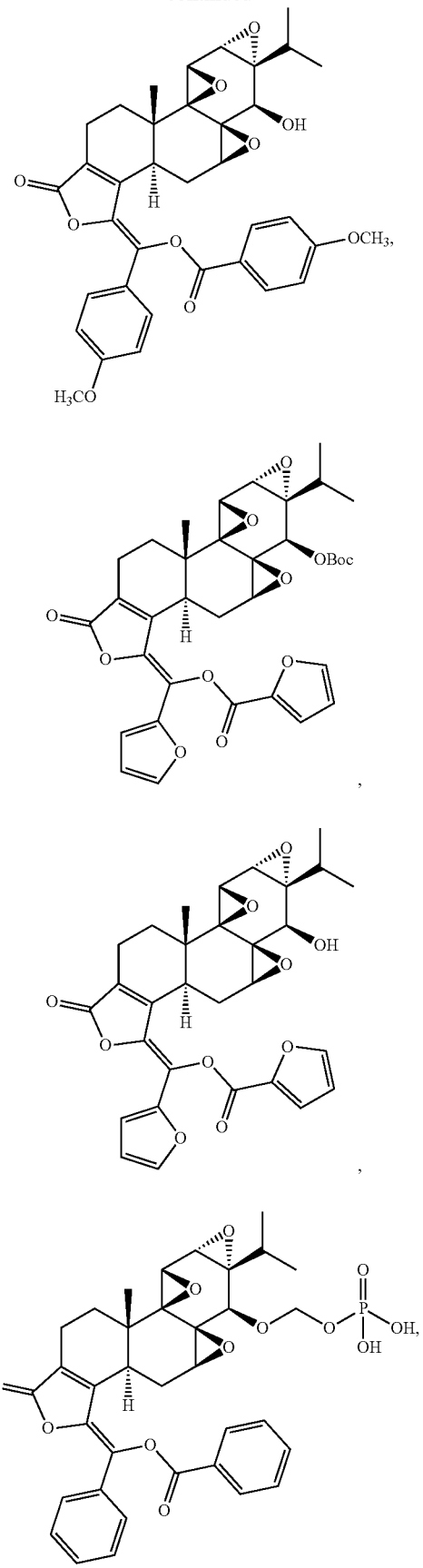

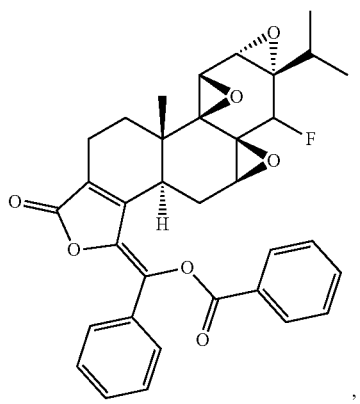

,

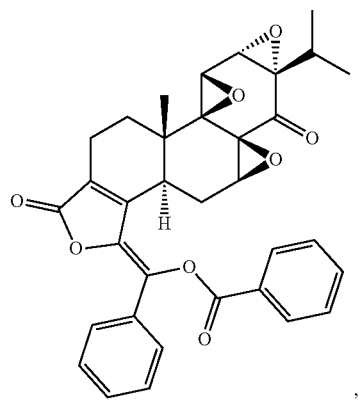

,

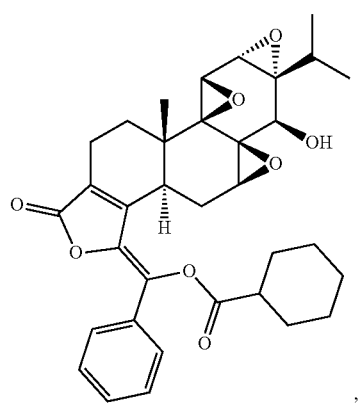

,

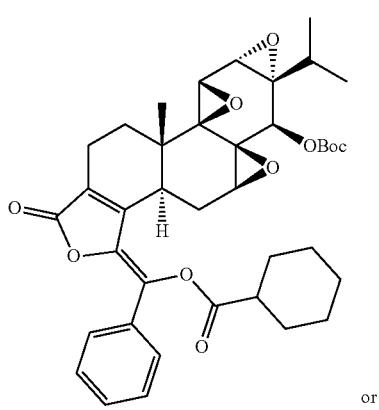

or

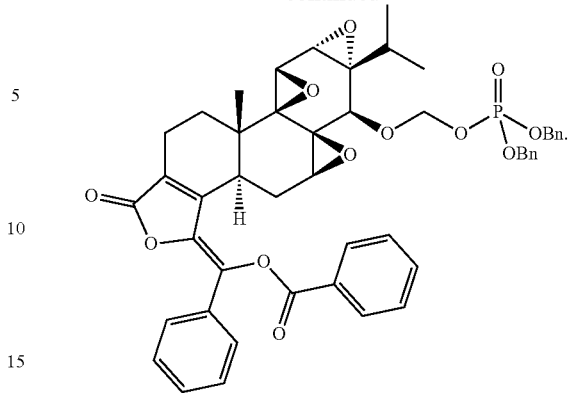

In the second aspect of the present invention, it provides a composition, wherein the composition comprises the compound, or the pharmaceutically acceptable salt, or enantiomer, diastereomer, tautomer, solvate, polymorph or prodrug thereof according to the first aspect; and an impurity, wherein, the content of the impurity is 0.1-2 wt %, preferably 0.2-1 wt %, and more preferably 0.3-0.6 wt %, based on the total weight of the composition.

In another preferred embodiment, the weight of the compound, or the pharmaceutically acceptable salt, or enantiomer, diastereomer, tautomer, solvate, polymorph or prodrug thereof according to the first aspect is 98% to 99.9% by weight, preferably 99 to 99.8% by weight, more preferably 99.2 to 99.6% by weight or 99.3 to 99.5% by weight, based on the total weight of the composition.

In the third aspect of the present invention, it provides a method for preparing the compound according to the first aspect, which comprises the following steps:

when $R_2$ is —C(=O)$R_4$ and $R_1$=$R_4$, the preparation method comprises the following steps:

reacting triptolide with an acylating agent, thereby obtaining a compound of formula II, and derivatizing the compound of formula II, thereby obtaining a compound of formula III; wherein the acylating agent is $R_1$COCl, $R_1$COBr or $R_1$COOCOR$_1$;

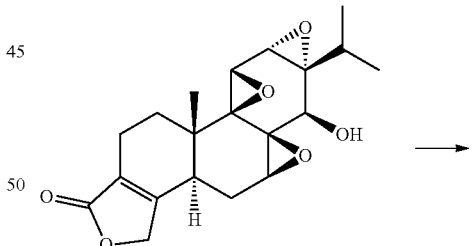

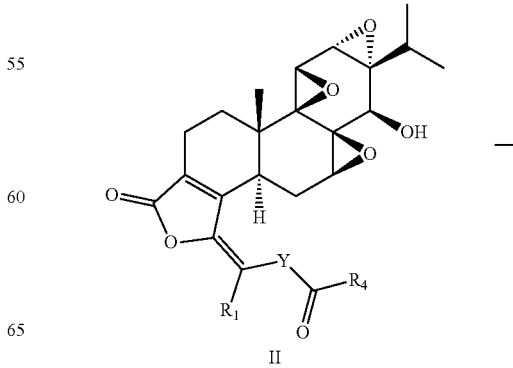

II

-continued

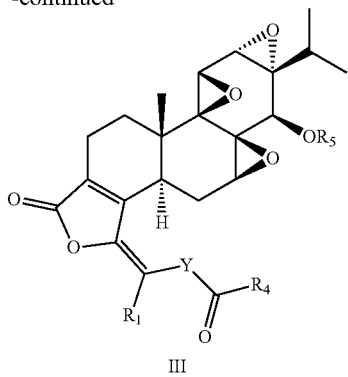

III or when $R_2$ is —C(=O)$R_4$ and $R_1 \neq R_4$, the preparation method comprises the following steps:

reacting triptolide with a first acylating reagent and a second acylating reagent respectively, thereby obtaining a compound of formula II, and deriving the compound of formula II, thereby obtaining a compound of formula III; wherein the first acylating agent is $R_1COCl$, $R_1COBr$ or $R_1COOCOR_1$, and the second acylating agent is $R_4COCl$, $R_4COBr$, or $R_4COOCOR_4$;

wherein, $R_1$, $R_4$, and $R_5$ are defined as in the first aspect.

The typical reaction steps are as follows:

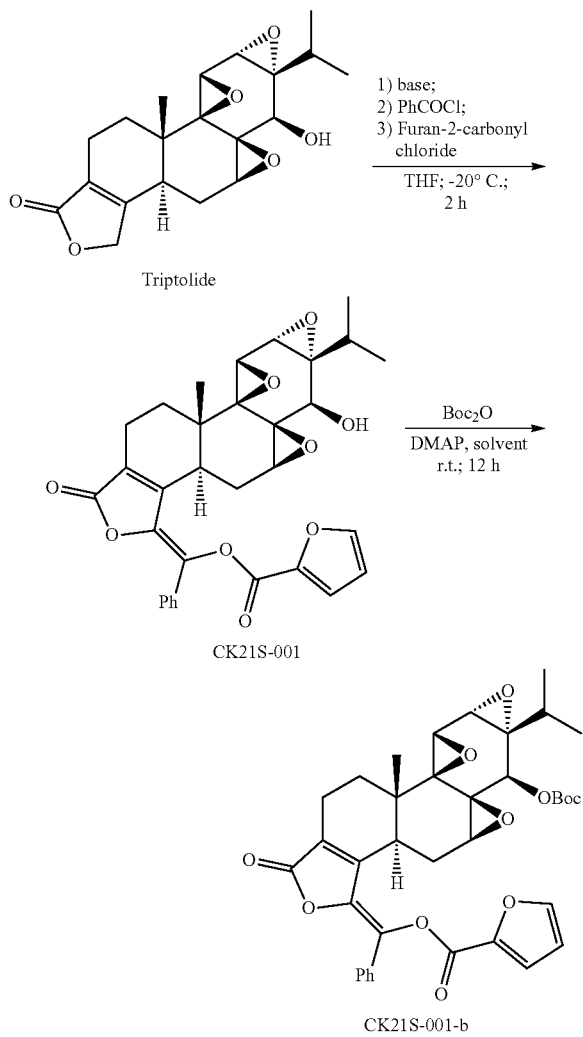

In the fourth aspect of the present invention, it provides a pharmaceutical composition, comprising:

the compound, or the pharmaceutically acceptable salt thereof, or the enantiomer, diastereomer, tautomer, solvate, polymorph or prodrug thereof according to the first aspect; and a pharmaceutically acceptable carrier.

In the fourth aspect of the present invention, it provides a use of the compound, or the pharmaceutically acceptable salt thereof, or the enantiomer, diastereomer, tautomer, solvate, polymorph or prodrug thereof according to the first aspect, or the pharmaceutical composition according to the third aspect, a) for preparation of a medicament for treating a tumor;
b) for preparation of a medicament for inducing apoptosis; and/or
c) for preparation of an immunosuppressive medicament.

In another preferred embodiment, the tumor is selected from the group consisting of leukemia, gastrointestinal stromal tumor, histiocytic lymphoma, non-small cell lung cancer, small cell lung cancer, pancreatic cancer, pulmonary squamous carcinoma, pulmonary adenocarcinoma, breast cancer, prostate cancer, liver cancer, skin cancer, epithelial cell cancer, cervical cancer, ovarian cancer, intestinal cancer, nasopharyngeal cancer, brain cancer, bone cancer, esophageal cancer, melanoma, kidney cancer, and oral cancer.

In another preferred embodiment, the tumor is preferably pancreatic cancer, prostate cancer, ovarian cancer or brain cancer.

It should be understood that, within the scope of the present invention, the above technical features of the present invention and the technical features specifically described in the following (such as the examples) can be combined with each other to form a new or preferred technical solution. Each feature disclosed in the description may be replaced by any alternative feature serving the same, equivalent, or similar purpose. Due to space limitations, it will not be redundantly described one by one.

DESCRIPTION OF EMBODIMENTS

Figure 1:
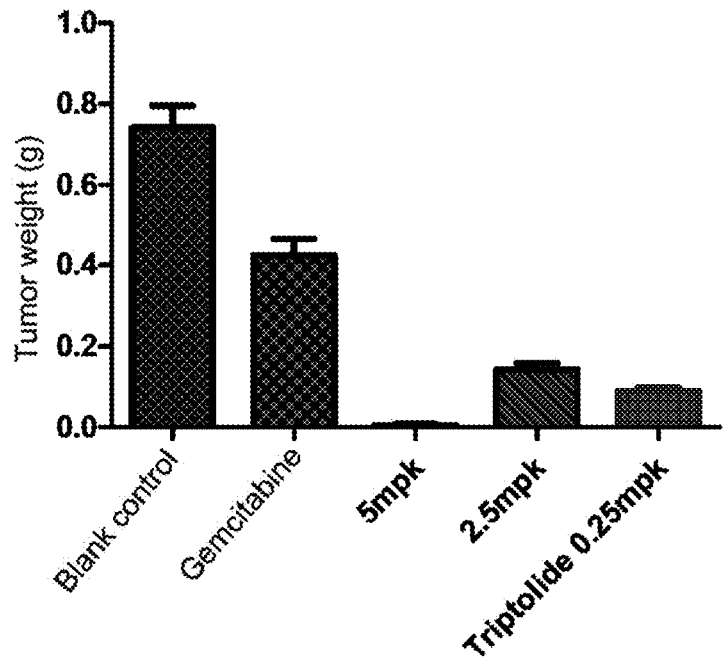
FIG. 1 is a graph showing a change of body weight in tumor-bearing mice over time.

After extensive and intensive research, the inventors of the present application have first introduced a modification group into triptolide through a C-19 double bond and, via further derivation, have obtained a series of novel triptolide derivatives with high activity (better immunosuppressive activity and antitumor activity) and high safety (low toxicity), which have a good prospect of development and application. Based on this, the present invention has been completed.

Term

Unless defined otherwise, all technical and scientific terms used herein have the same meaning as commonly understood by one of ordinary skill in the art to which the subject matter of the claims belongs. Unless otherwise stated, all patents, patent applications, and published materials cited herein are incorporated by reference in their entirety.

It is to be understood that the foregoing brief description and the following detailed description are exemplary and are for explanation only. They do not place any limitation on the subject matter of the invention. In this application, the use of the singular includes the plural unless specifically stated otherwise. It must be noted that, unless the context clearly indicates, otherwise the singular forms used in the specification and claims include the plural forms of the referenced things. It should also be noted that "or" is used to mean "and/or" unless stated otherwise. Furthermore, the terms "comprise" and other forms such as "include", "contain", and "comprising" are not limitative.

Definitions of standard chemical terms can be found in the references. Unless otherwise stated, conventional methods within the skill of the art, such as mass spectrometry, NMR, IR, and UV/VIS spectroscopy and pharmacological methods, are used. Unless specifically defined, the terms used herein in related descriptions of analytical chemistry, organic synthetic chemistry, pharmacology and medicinal chemistry are known in the art. Standard techniques can be used in chemical synthesis, chemical analysis, drug preparation, formulation and delivery, and treatment of patients. For example, the manufacturer's instructions for use of the kit can be used, or the reaction and purification can be performed in a manner known in the art or according to the description of the present invention. The techniques and methods described above can generally be implemented according to conventional methods well known in the art, based on descriptions in several summary and more specific documents cited and discussed in this specification. In this specification, groups and the substituents thereof may be selected by those skilled in the art to provide stable moieties and compounds.

When a substituent is described by a conventional chemical formula written from left to right, the substituent also includes a chemically equivalent substituent obtained when the structural formula is written from right to left. For example, —CH$_2$O— is equivalent to —OCH$_2$—.

The section headings used herein are for organizational purposes only and should not be construed as limiting the subject matter. All documents or parts of documents cited in this application include but are not limited to patents, patent applications, articles, books, operating manuals and papers, which are incorporated herein by reference in their entirety.

The total number of carbon atoms present in the group is indicated by a simplified symbol in front of certain chemical groups defined herein. For example, C1-6 alkyl refers to an alkyl group, as defined below, having a total of 1 to 6 carbon atoms. The total number of carbon atoms in the simplified symbol does not include carbons that may be present in a substituent of the group.

In addition to the foregoing, when used in the description and claims of this application, the following terms have the following meanings unless otherwise specified.

In the present application, the term "halogen" refers to fluorine, chlorine, bromine or iodine.

"Hydroxy" refers to —OH.

"Hydroxyalkyl" refers to an alkyl group, as defined below, substituted with a hydroxy (—OH).

"Carbonyl" refers to —C(=O)—.

"Nitro" refers to —NO$_2$.

"Cyano" refers to —CN.

"Amino" refers to —NH$_2$.

"Substituted amino" refers to an amino group substituted with one or two alkyl, alkylcarbonyl, aralkyl, and heteroaralkyl, as defined below, for example, monoalkylamino, dialkylamino, alkylamido, aralkylamino, heteroaralkylamino.

"Carboxy" means —COOH.

In the present application, as a group or part of other group (for example, used in a group such as a halogen-substituted alkyl), the term "alkyl" means a straight or branched hydrocarbon chain group without unsaturated bond which is composed of only carbon atoms and hydrogen atom and has, for example, 1 to 12 (preferably 1 to 8, more preferably 1 to 6) carbon atoms and connects to the rest of the molecule through a single bond. Examples of alkyl include, but are not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl, decyl and the like.

In the present application, as a group or part of other group, the term "alkenyl" means a straight or branched hydrocarbon chain group which is composed of only carbon atoms and hydrogen atoms, contains at least one double bond, has, e.g., 2 to 14 (preferably 2 to 10, more preferably 2 to 6) carbon atoms and attaches to the rest of the molecule through a single bond, such as, but not limited to, vinyl, propenyl, allyl, but-1-enyl, but-2-enyl, pent-1-enyl, pent-1,4-dienyl and the like.

In the present application, as a group or part of other group, the term "alkynyl" means a straight or branched hydrocarbon chain group which is composed of only carbon atoms and hydrogen atoms, contains at least one triple bond, has, e.g., 2 to 14 (preferably 2 to 10, more preferably 2 to 6) carbon atoms and attaches to the rest of the molecule through a single bond, such as, but not limited to, ethynyl, prop-1-ynyl, but-1-ynyl, pent-1-en-4-ynyl and the like.

In the present application, as a group or part of other group, the term "cycloalkyl" means a stable non-aromatic monocyclic or polycyclic hydrocarbon group which is composed of only carbon atoms and hydrogen atoms, may include fused ring system, bridged ring system or spiro ring system, has 3 to 15 carbon atoms, preferably 3 to 10 carbon atoms, and more preferably 3 to 8 carbon atoms, and are saturated or unsaturated and connects to the rest of the molecule by a single bond through any suitable carbon atom.

Unless otherwise specifically stated in this specification, the carbon atoms in a cycloalkyl group may be optionally oxidized. Examples of cycloalkyl include, but are not limited to, cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-dihydroindenyl, 1,2,3,4-tetrahydro-naphthyl, 5,6,7,8-tetrahydro-naphthyl, 8,9-dihydro-7H-benzo-cyclohepten-6-yl, 6,7,8,9-tetrahydro-5H-benzo-cycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-cyclopentadienyl and the like.

In the present application, as a group or part of other group, the term "heterocyclyl" means a stable 3- to 20-membered non-aromatic cyclic group consisting of 2 to 14 carbon atoms and 1 to 6 heteroatoms selected from nitrogen, phosphorus, oxygen, and sulfur. Unless otherwise stated in this specification, a heterocyclyl may be a monocyclic, bicyclic, tricyclic, or more cyclic ring system, which may include a fused ring system, a bridged ring system, or a spiro ring system; the nitrogen, carbon or sulfur atoms may be optionally oxidized; the nitrogen atoms may be optionally quaternized; and heterocyclyl may be partially or fully saturated. Heterocyclyl can be attached to the rest of the molecule via a carbon or heteroatom and via a single bond.

In a fused ring-containing heterocyclyl, one or more rings may be an aryl or heteroaryl group as defined below, provided that the point of attachment to the rest of the molecule is a non-aromatic ring atom. For the purpose of the present invention, the heterocyclyl is preferably a stable 4- to 11-membered non-aromatic monocyclic, bicyclic, bridged, or spirocyclic group containing 1 to 3 heteroatoms selected from nitrogen, oxygen, and sulfur, more preferably a stable 4- to 8-membered non-aromatic monocyclic, bicyclic, bridged, or spirocyclic group containing 1 to 3 heteroatoms selected from nitrogen, oxygen, and sulfur. Examples of heterocyclyl include, but are not limited to: pyrrolidinyl, morpholinyl, piperazinyl, homopiperazinyl, piperidinyl, thiomorpholinyl, 2,7-diaza-spiro[3.5]non-7-yl, 2-oxa-6-azaspiro[3.3]hept-6-yl, 2,5-diaza-bicyclo[2.2.1] hept-2-yl, azacyclobutyl, pyranyl, tetrahydropyranyl, thioranyl, tetrahydrofuryl, oxazinyl, dioxocyclopentyl, tetrahydroisoquinolinyl, decahydroisoquinolinyl, imidazolinyl, imidazolidinyl, quinolizidyl, thiazolidinyl, isothiazolidinyl, isoxazolidinyl, dihydroindolyl, octahydroindolyl, octahydroisoindolyl, pyrrolidinyl, pyrazolidinyl, phthalimide and the like.

In the present application, as a group or part of other group, the term "aryl" means a conjugated hydrocarbon ring system group having 6 to 18 carbon atoms, preferably 6 to 10 carbon atoms. For the purpose of the present invention, the aryl may be a monocyclic, bicyclic, tricyclic or more cyclic ring system, and may also be fused with a cycloalkyl or heterocyclyl as defined above, provided that the aryl is connected to the rest of the molecule by a single bond via an atom on the aromatic ring. Examples of aryl include, but are not limited to, phenyl, naphthyl, anthracenyl, phenanthryl, fluorenyl, 2,3-dihydro-1H-isoindolyl, 2-benzoxazolinone, 2H-1,4-benzoxazin-3(4H)-one-7-yl and the like.

In the present application, the term "arylalkyl" refers to an alkyl as defined above which is substituted with an aryl as defined above.

In the present application, as a group or part of other group, the term "heteroaryl" means a 5- to 16-membered conjugated ring system group having 1 to 15 carbon atoms (preferably having 1 to 10 carbon atoms) and 1 to 6 heteroatoms selected from nitrogen, oxygen, and sulfur. Unless otherwise stated in this specification, a heteroaryl may be a monocyclic, bicyclic, tricyclic, or more cyclic ring system, and may be fused with a cycloalkyl or heterocyclyl as defined above, provided that heteroaryl is connected to the rest of the molecule by a single bond via an atom on the aromatic ring. The nitrogen, carbon or sulfur atom in heteroaryl can be optionally oxidized; and the nitrogen atom can be optionally quaternized. For the purpose of the present invention, the heteroaryl is preferably a stable 5- to 12-membered aromatic group containing 1 to 5 heteroatoms selected from nitrogen, oxygen, and sulfur, and more preferably a stable 5- to 10-membered aromatic group containing 1 to 4 heteroatoms selected from nitrogen, oxygen and sulfur, or a stable 5- to 6-membered aromatic group containing 1 to 3 heteroatoms selected from nitrogen, oxygen, and sulfur. Examples of heteroaryl include, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzoimidazolyl, benzopyrazolyl, indolyl, furyl, pyrrolyl, triazolyl, tetrazolyl, triazinyl, indolizinyl, isoindolyl, indazolyl, isoindazolyl, purinyl, quinolinyl, isoquinolinyl, diazonaphthyl, naphthyridinyl, quinoxalinyl, pteridinyl, carbazolyl, carbolinyl, phenanthridinyl, phenanthrolinyl, acridinyl, phenazinyl, isothiazolyl, benzothiazolyl, benzothienyl, oxatriazolyl, cinnolinyl, quinazolinyl, phenylthio, purocolinyl, o-diazaphenanthryl, isoxazolyl, phenoxazinyl, phenothiazinyl, 4,5,6,7-tetrahydrobenzo[b]thienyl, naphthopyridyl, [1,2,4]triazolo[4,3-b]pyridazine, [1,2,4]triazolo [4,3-a]pyrazine, [1,2,4]triazolo[4,3-c]pyrimidine, [1,2,4]triazolo [4,3-a]pyridine, imidazo[1,2-a]pyridine, imidazo[1,2-b]pyridazine, imidazo[1,2-a]pyrazine and the like.

In the present application, the term "heteroarylalkyl" refers to an alkyl as defined above, which is substituted with a heteroaryl as defined above.

In the present application, "optional" or "optionally" means that the event or condition described later may or may not occur, and the description includes both the occurrence or non-occurrence of the event or condition. For example, "optionally substituted aryl" means that the aryl is substituted or unsubstituted, and the description includes both a substituted aryl and an unsubstituted aryl.

As used herein, the terms "moiety", "structural moiety", "chemical moiety", "group" and "chemical group" refer to a particular fragment or functional group in a molecule. A chemical moiety is generally considered as a chemical entity that is embedded or attached to a molecule.

"Stereoisomer" refers to a compound that is composed of the same atoms and is bonded by the same bond, but has different three-dimensional structure. The invention will cover various stereoisomers and mixtures thereof.

When the compound of the present invention contains an olefinic double bond, the compound of the present invention is intended to include E- and Z-geometric isomers, unless otherwise stated.

"Tautomer" refers to an isomer formed by the transfer of a proton from one atom of a molecule to another atom of the same molecule. All tautomeric forms of the compounds of the invention will also be included within the scope of the invention.

The compounds of the invention, or the pharmaceutically acceptable salts thereof, may contain one or more chiral carbon atoms, and may thus produce enantiomers, diastereomers and other stereoisomeric forms. Each chiral carbon atom can be defined as (R)- or (S)-based on stereochemistry. The invention is intended to include all possible isomers, as well as their racemates and optically pure forms. The compounds of the present invention can be prepared by using racemates, diastereomers or enantiomers as raw materials or intermediates. Optically active isomers can be prepared using chiral synthons or chiral reagents, or resolved using conventional techniques, such as crystallization, chiral chromatography and the like.

Conventional techniques for the preparation/isolation of individual isomers include chiral synthesis from suitable optically pure precursors, or resolution of the racemates (or the racemates of salts or derivatives) using, for example, chiral high performance liquid chromatography.

In the present application, the term "pharmaceutically acceptable salt" includes pharmaceutically acceptable acid addition salts and pharmaceutically acceptable base addition salts.

"Pharmaceutically acceptable acid addition salt" refers to a salt formed with an inorganic or organic acid that retains the biological effectiveness of the free base without other side effects. Inorganic acid salts include, but are not limited to, hydrochloride, hydrobromide, sulfate, nitrate, phosphate, etc.; organic acid salts include, but are not limited to, formate, acetate, 2,2-dichloroacetate, trifluoroacetate, propionate, hexanoate, octanoate, decanoate, undecylenate, glycolate, gluconate, lactate, sebacate, adipate, glutarate, malonate, oxalate, maleate, succinate, fumarate, tartrate, citrate, palmitate, stearate, oleate, cinnamate, laurate, malate, glutamate, pyroglutamate, aspartate, benzoate, mesylate, benzenesulfonate, p-toluenesulfonate, alginate, ascorbate, salicylate, 4-aminosalicylate, naphthalene disulfonate and the like. These salts can be prepared by methods known in the art.

"Pharmaceutically acceptable base addition salt" refers to a salt formed with an inorganic or organic base capable of maintaining the biological effectiveness of the free acid without other side effects. Salts derived from inorganic bases include, but are not limited to, sodium, potassium, lithium, ammonium, calcium, magnesium, iron, zinc, copper, manganese, aluminum salt, and the like. Preferred inorganic salts are ammonium, sodium, potassium, calcium and magnesium salts. Salts derived from organic bases include, but are not limited to, the following salts: primary, secondary, and tertiary amines, substituted amines, including natural substituted amines, cyclic amines, and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, bicyclohexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin and the like. Preferred organic bases include isopropylamine, diethylamine, ethanolamine, trimethylamine, dicyclohexylamine, choline, and caffeine. These salts can be prepared by methods known in the art.

"Polymorph" refers to different solid crystalline phases of a certain compound of the present invention due to the presence of two or more different molecular arrangements in the solid state. Certain compounds of the invention may exist in more than one crystalline form, and the invention is intended to include various crystalline forms and mixtures thereof.

Generally, crystallization will produce a solvate of the compound of the invention. The term "solvate" as used in the present invention refers to an aggregate comprising one or more compound molecules of the present invention and one or more solvent molecules. The solvent may be water, and the solvate in this case is a hydrate. Alternatively, the solvent may be an organic solvent. Thus, the compounds of the present invention may exist as hydrates, including monohydrates, dihydrates, hemihydrates, sesquihydrates, trihydrates, tetrahydrates, and the like, as well as the corresponding solvated forms. The compounds of the present invention can form true solvates, but in some cases it is also possible to keep only unstable water or a mixture of partially unstable solvent and water. The compounds of the present invention can be reacted in a solvent or precipitated or crystallized from the solvent. Solvates of the compounds of the invention are also included within the scope of the invention.

The invention also includes prodrugs of the aforementioned compounds. In the present application, the term "prodrug" means a compound that can be converted into a biologically active compound of the invention under physiological conditions or by solvolysis. Accordingly, the term "prodrug" refers to a pharmaceutically acceptable metabolic precursor of the compound of the invention. When administered to an individual in need, the prodrug may not be active, but is transformed in vivo into the active compound of the invention. Prodrugs are usually rapidly transformed in the body to produce the parent compound of the invention, for example, by hydrolysis in blood. Prodrug compounds typically provide the advantages of solubility, histocompatibility, or sustained release in mammalian organisms. Prodrugs include known amino protecting groups and carboxy protecting groups.

In the present application, "pharmaceutical composition" refers to a formulation of the compound of the present invention and a medium generally accepted in the art for delivering a biologically active compound to a mammal (e.g., a human). The medium includes a pharmaceutically acceptable carrier. The purpose of the pharmaceutical composition is to promote the administration in the organism, which is beneficial to the absorption of the active ingredient and then exerts the biological activity.

The term "pharmaceutically acceptable" as used herein refers to a substance (such as a carrier or diluent) that does not affect the biological activity or property of the compounds of the present invention, and is relatively non-toxic, i.e., the substance can be administered to an individual without causing adverse biological reactions or interact with any of the components contained in the composition in an undesirable manner.

In the present application, "pharmaceutically acceptable carrier" includes, but is not limited to, any adjuvant, carrier, excipient, glidant, sweetener, diluent, preservative, dye/colorant, flavoring agent, surfactant, wetting agent, dispersant, suspending agent, stabilizer, isotonic agent, solvent or emulsifier approved by the relevant government authority as acceptable for human or livestock use.

The "tumor" and "abnormal cell proliferation-related diseases" described in the present invention include, but are not limited to, leukemia, gastrointestinal stromal tumor, histiocytic lymphoma, non-small cell lung cancer, small cell lung cancer, pancreatic cancer, pulmonary squamous carcinoma, pulmonary adenocarcinoma, breast cancer, prostate cancer, liver cancer, skin cancer, epithelial cancer, cervical cancer, ovarian cancer, bowel cancer, nasopharyngeal cancer, brain cancer, bone cancer, esophageal cancer, melanoma, kidney cancer, oral cancer and the like.

As used herein, the terms "preventive", "prevent", and "prevention" include enabling a patient to reduce the likelihood of the occurrence or worsening of a disease or disorder.

As used herein, the term "treatment" and other similar synonyms include the following meanings:

(i) preventing the occurrence of a disease or condition in mammals, especially when such mammals are susceptible to the disease or disorder but have not been diagnosed as having the disease or disorder;

(ii) inhibiting a disease or disorder, i.e., curbing the disease development;

(iii) alleviating a disease or disorder, i.e., regressing the state of the disease or disorder; or (iv) reducing symptoms caused by the disease or disorder.

As used herein, the terms "effective amount", "therapeutically effective amount", or "pharmaceutically effective amount" refers to the amount of at least one agent or compound sufficient to relieve one or more symptoms of the disease or disorder being treated to a certain extent after it is administered. The result can be the reduction and/or alleviation of signs, symptoms or causes, or any other desired change in the biological system. For example, an "effective amount" for use in therapy is the amount of a composition comprising a compound disclosed herein that is required to provide a significant clinically alleviating effect on a symptom. The effective amount suitable for any individual case can be determined using techniques such as a dose escalation test.

As used herein, the terms "administer", "administering", "administration" and the like refer to a method capable of delivering a compound or composition to a desired site for a biological effect. These methods include, but are not limited to, the oral route, the duodenal route, parenteral injections (including intravenous, subcutaneous, intraperitoneal, intramuscular, intraarterial injection or infusion), topical administration, and rectal administration. Those skilled in the art are familiar with administration techniques that can be used in the compounds and methods described herein. In a preferred embodiment, the compounds and compositions discussed herein are administered orally.

As used herein, the terms "pharmaceutical combination", "drug combination", "combined administration of other treatments", "administration of other therapeutic agents", and the like refer to a drug treatment obtained by mixing or combining more than one active ingredient, including fixed and unfixed combinations of active ingredients. The term "fixed combination" refers to the simultaneous administration of at least one compound described herein and at least one synergistic agent to a patient in the form of a single entity or a single dosage form. The term "unfixed combination" refers to the simultaneous, combined, or sequential administration of at least one compound described herein and at least one synergistic formulation to a patient in the form of separate entities. These also apply to cocktail therapies, for example the administration of three or more active ingredients.

Those skilled in the art will also understand that in the methods described below, the functional groups of the intermediate compounds may need to be protected by a suitable protecting group. Such functional groups include hydroxyl, amino, mercapto, and carboxylic acids. Suitable hydroxy protecting groups include trialkylsilyl or diarylalkylsilyl (e.g. tert-butyldimethylsilyl, tert-butyldiphenylsilyl or trimethylsilyl), tetrahydropyranyl, benzyl and the like. Suitable protecting groups for amino, guanyl and guanidino include tert-butoxycarbonyl, benzyloxycarbonyl and the like. Suitable thiol-protecting groups include —C(O)—R″ (wherein R″ is alkyl, aryl, or aralkyl), p-methoxybenzyl, trityl and the like. Suitable carboxy protecting groups include alkyl, aryl or aralkyl esters.

Protecting groups can be introduced and removed according to standard techniques known to those skilled in the art and as described herein. The protective group may also be a polymer resin.

The present invention will be further described below with reference to specific examples. It should be understood that these examples are only used to illustrate the present invention and not to limit the scope of the present invention. The experimental methods without specific conditions in the following examples are generally performed according to conventional conditions (such as the conditions described in Sambrook et al., Molecular Cloning: Laboratory Manual (New York: Cold Spring Harbor Laboratory Press, 1989)) or according to conditions recommended by the manufacturer. Unless stated otherwise, percentages and parts are percentages by weight and parts by weight.

Unless otherwise defined, all professional and scientific terms used herein have the same meaning as those familiar to those skilled in the art. In addition, any methods and materials similar or equal to those described can be used in the method of the present invention. The preferred embodiments and materials described herein are for demonstration purposes only.

Example 1: Preparation of Compound CK21S-001

1.1 Synthesis of Compound CK21S-001

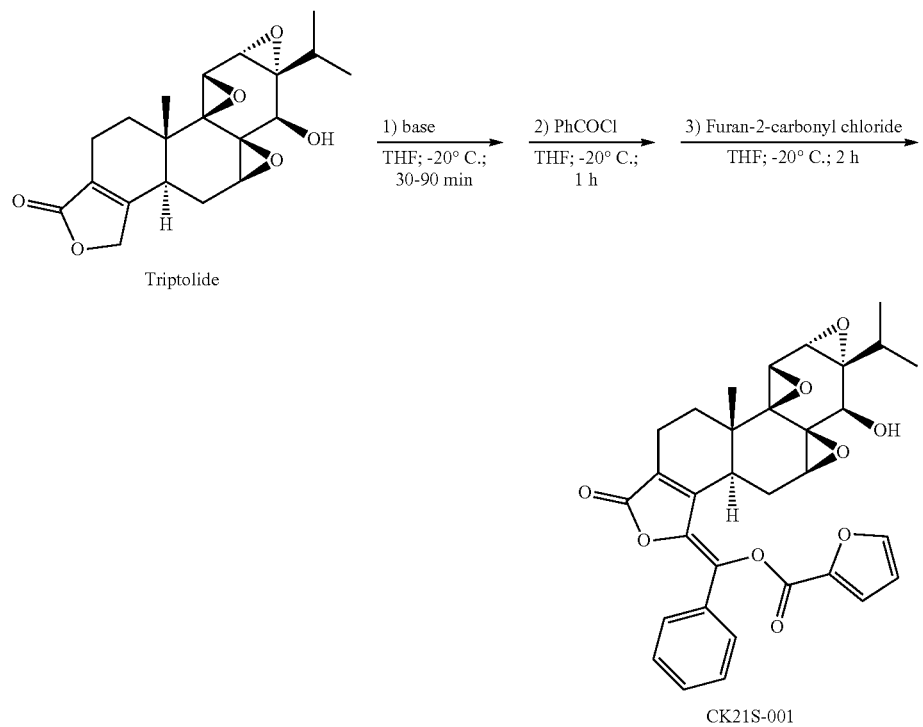

Under nitrogen protection, the compound triptolide (180 mg, 0.5 mmol) was added into a three-necked round bottom flask, anhydrous tetrahydrofuran (25 mL) was added, the temperature of mixture was lowered to −20° C., and a solution of lithium 2,2,6,6-tetramethylpiperidine in tetrahydrofuran/toluene (0.75 mL, 2.0M, 1.5 mmol) at this temperature. After the mixture was stirred at this temperature for 30 min, benzoyl chloride (0.105 mL, 0.75 mmol) was slowly added dropwise. After the dropwise addition, the mixture was stirred and reacted for 1 h and then 2-furoyl chloride (0.105 mL, 0.75 mmol) was added dropwise. The mixture was stirred at −20° C. and reacted for 2 h. The reaction was quenched by adding aqueous sodium carbonate (10%), and the mixture was extracted with ethyl acetate (25 mL×3). The organic phases were combined, dried over anhydrous sodium sulfate, and concentrated under reduced pressure. The crude product was separated and purified by silica gel chromatography (dichloromethane: ethyl acetate), and the target product (white solid, 255 mg, yield 90%) was collected and further recrystallized in a mixed organic solvent to obtain a final product (213 mg, yield 85%, purity >99%).

$^1$H NMR (400 MHz, CDCl$_3$): δ 7.76 (d, J=1.6 Hz, 1H), 7.74 (d, J=1.2 Hz, 2H), 7.54 (dd, J$_1$=0.8 Hz, J$_2$=3.6 Hz, 1H), 7.44~7.36 (m, 3H), 6.63 (dd, J$_1$=1.6 Hz, J$_2$=3.6 Hz, 1H), 3.79 (d, J=2.8 Hz, 1H), 3.40 (d, J=2.4 Hz, 1H), 3.17 (d, J=9.2 Hz, 1H), 2.97~2.89 (m, 2H), 2.63~2.56 (m, 2H), 2.37~2.33 (m, 2H), 2.21 (q, J=6.4 Hz, 1H), 1.93 (t, J=13.6 Hz, 1H), 1.57 (s, 3H), 1.56~1.51 (m, 1H), 1.43 (s, 3H), 1.12 (s, 3H), 1.15~1.08 (m, 1H), 0.96 (d, J=7.2 Hz, 3H), 0.84 (d, J=7.2 Hz, 3H). $^{13}$C NMR (100 MHz, CDCl$_3$): δ 171.3, 167.9, 155.9, 151.4, 150.5, 148.2, 142.7, 142.3, 134.6, 132.4, 131.5, 129.9, 129.5, 129.1, 128.9, 128.6, 128.0, 121.5, 113.3, 112.6, 73.1, 60.0, 65.6, 65.4, 60.7, 56.9, 56.4, 56.3, 53.9, 40.8, 36.7, 35.9, 30.1, 29.1, 27.9, 24.6, 17.8, 17.7, 16.8, 14.8. MS calcd for C$_{32}$H$_{30}$O$_9$ (M+): 559.2, found 559.2.

1.2 Synthesis of Compound CK21S-001-b

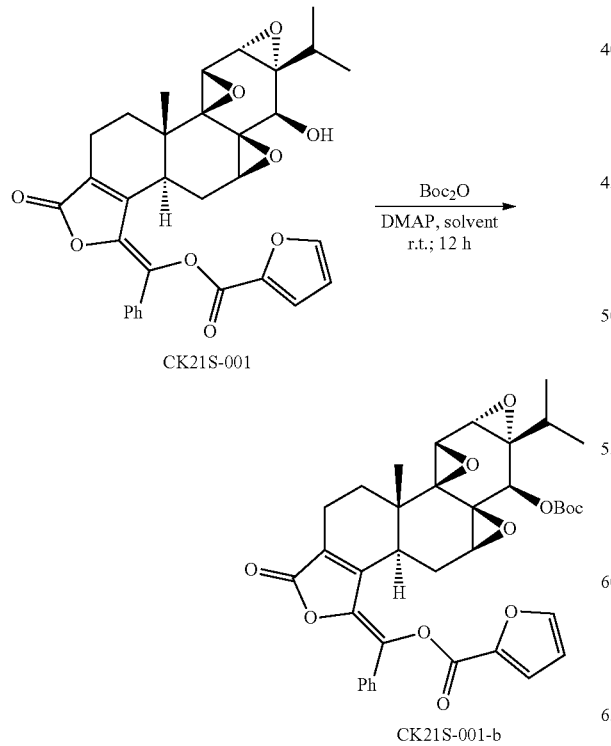

At room temperature, CK21S-001 (558 mg, 1 mmol) was loaded into a dry round bottom flask, and 10 mL of ethyl acetate was added. After dissolution, N,N-dimethylpyridine (DMAP, 0.6 g, 5 mmol) and di-tert-butyl dicarbonate (0.65 g, 3 mmol) were separately added and the mixture was reacted at room temperature overnight. After the reaction was completed, the mixture was diluted with ethyl acetate (150 mL), and the organic phase was washed with dilute hydrochloric acid (50 mL), water (50 mL) and saturated sodium chloride (10 mL), dried over anhydrous sodium sulfate, filtered, and concentrated under reduced pressure. The crude product was separated and purified by silica gel chromatography (n-hexane: ethyl acetate), and the target product was collected (white solid, 0.6 g, 90%, purity >98%).

$^1$H NMR (400 MHz, CDCl$_3$): δ 7.77 (d, J=0.8 Hz, 2H), 7.75 (dd, J$_1$=2.0 Hz, J$_2$=3.2 Hz, 1H), 7.54 (dd, J=0.8 Hz, J$_2$=3.6 Hz, 1H), 7.44~7.36 (m, 3H), 6.65 (dd, J=1.6 Hz, J$_2$=3.6 Hz, 1H), 4.53 (s, 1H), 4.12 (q, J=7.2 Hz, 1H), 3.702 (d, J=2.8 Hz, 1H), 3.41 (d, J=2.4 Hz, 1H), 3.03 (d, J=6.0 Hz, 1H), 3.94~2.88 (m, 1H), 2.56~2.52 (m, 1H), 2.39~2.31 (m, 2H), 1.94~1.86 (m, 2H), 1.60 (s, 3H), 1.58~1.50 (m, 1H), 1.49 (s, 9H), 1.33~1.24 (m, 4H), 1.13 (s, 3H), 1.15~1.08 (m, 1H), 0.96 (d, J=5.6 Hz, 3H), 0.88 (t, J=7.2 Hz, 3H), 0.82 (d, J=6.8 Hz, 3H). MS calcd for C$_{37}$H$_{38}$O$_{11}$ (M+): 659.2, found 659.2.

Example 2: Preparation of Compound CK21S-002

2.1 Synthesis of Compound CK21S-002

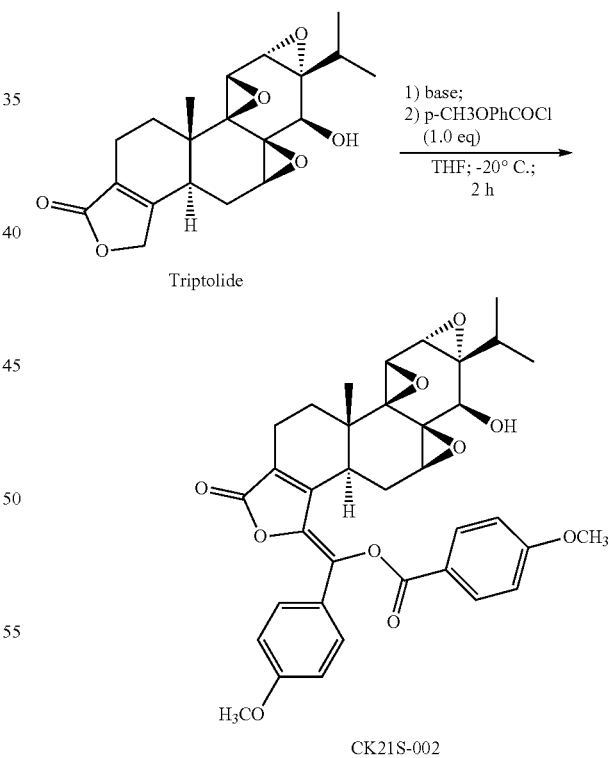

CK21S-002 was prepared by using a similar method for preparation of CK21S-001, with a yield of 89% and a purity of greater than 99%. The difference was that p-methoxybenzoyl chloride was used in place of benzoyl chloride and furoyl chloride in Example 1, and the other conditions were the same.

¹H NMR (400 MHz, CDCl₃): δ 8.20 (d, J=8.8 Hz, 2H), 7.71 (d, J=8.8 Hz, 2H), 7.03 (d, J=8.8 Hz, 2H), 6.92 (d, J=8.8 Hz, 2H), 3.87 (s, 3H), 3.83 (s, 3H), 3.79 (d, J=3.2 Hz, 1H), 3.37 (d, J=3.2 Hz, 1H), 3.02 (d, J=9.6 Hz, 1H), 2.84~2.78 (m, 1H), 2.71 (d, J=6.4 Hz, 1H), 2.59~2.53 (m, 2H), 2.35~2.32 (m, 2H), 2.19~2.12 (m, 1H), 1.92~1.85 (m, 1H), 1.53~1.50 (m, 1H), 1.15 (s, 3H), 1.12~1.09 (m, 1H), 0.90 (d, J=6.8 Hz, 3H), 0.81 (d, J=6.8 Hz, 3H). ¹³C NMR (100 MHz, CDCl₃): δ 168.3, 164.6, 164.1, 160.7, 150.4, 141.2, 133.6, 132.7, 132.7, 129.8, 129.8, 127.7, 124.5, 120.2, 114.4, 114.4, 114.1, 114.1, 72.9, 65.9, 65.3, 60.8, 60.1, 56.5, 55.5, 55.4, 53.7, 40.7, 36.7, 29.3, 28.0, 24.6, 17.6, 17.5, 16.7, 15.0. MS calcd for C₃₆H₃₆O₁₀ (M+): 629.3, found 629.3.

2.2 Synthesis of Compound CK21S-002-b

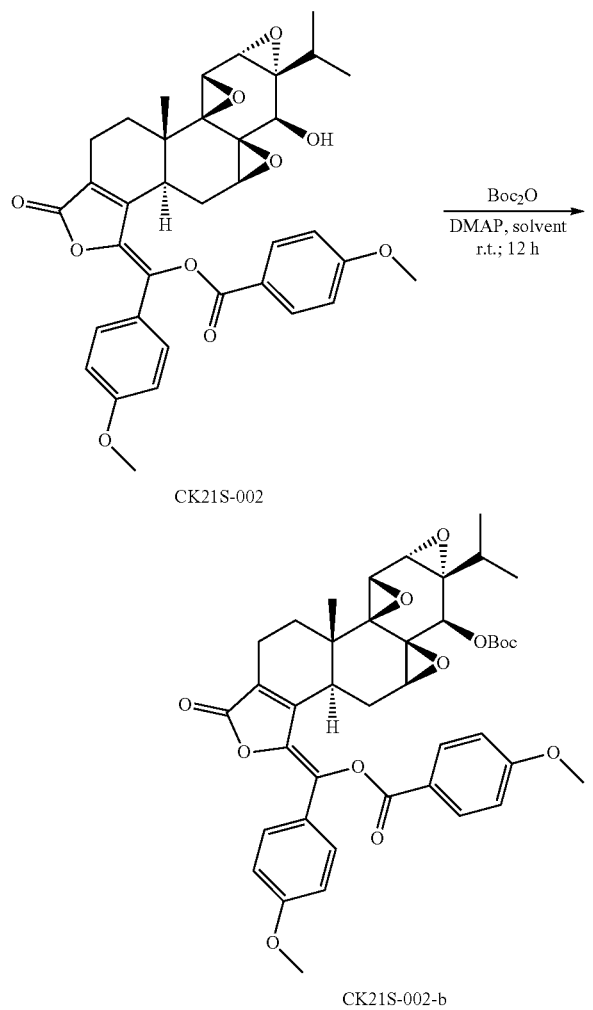

CK21S-002-b was prepared from CK21S-001-a by using a similar method for preparation of CK21S-001-b, with a yield of 90% and a purity of more than 99%.

¹H NMR (400 MHz, CDCl₃): δ 8.21 (d, J=8.8 Hz, 2H), 7.72 (d, J=9.2 Hz, 2H), 7.05 (d, J=9.2 Hz, 2H), 6.92 (d, J=8.8 Hz, 2H), 4.35 (s, 1H), 3.89 (d, J=6 Hz, 1H), 3.88 (s, 3H), 3.83 (s, 3H), 3.70 (d, J=3.2 Hz, 1H), 3.38 (d, J=2.8 Hz, 1H), 2.80~2.78 (m, 2H), 2.55~2.52 (m, 1H), 2.34~2.30 (m, 2H), 1.91~1.80 (m, 2H), 1.47 (s, 9H), 1.11 (s, 3H), 1.12~1.05 (m, 1H), 0.89 (d, J=6.8 Hz, 3H), 0.79 (d, J=6.8 Hz, 3H). MS calcd for C₄₁H₄₄O₁₂ (M+): 729.3, found 729.3.

Example 3: Preparation of Compound CK21S-003

3.1 Synthesis of Compound CK21S-003

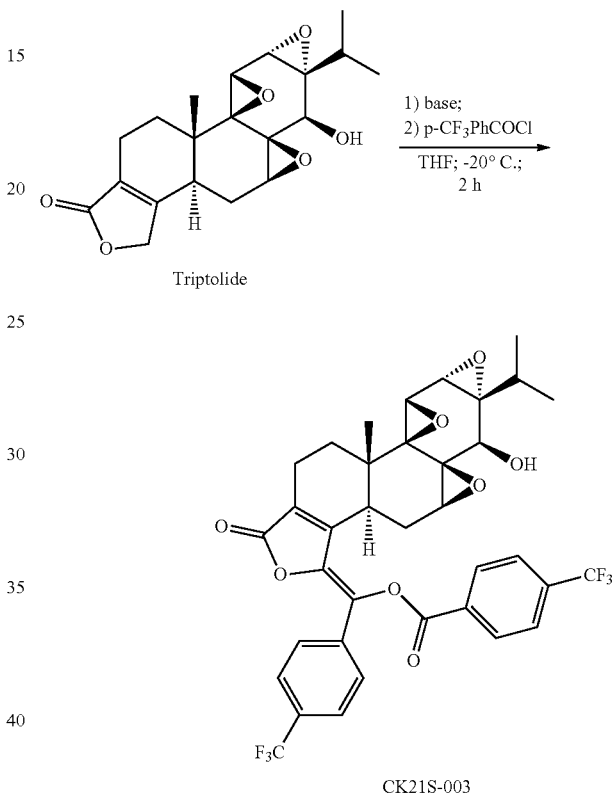

CK21S-003 was prepared by using a similar method for preparation of CK21S-001, with a yield of 90% and a purity of greater than 99%. The difference was that p-trifluoromethylbenzoyl chloride was used in place of benzoyl chloride and furoyl chloride in example 1, and the other conditions were the same.

¹H NMR (400 MHz, CDCl₃): δ 8.36 (d, J=8.0 Hz, 2H), 7.88 (d, J=8.0 Hz, 2H), 7.81 (d, J=8.0 Hz, 2H), 7.67 (d, J=8.0 Hz, 2H), 3.82 (d, J=3.2 Hz, 1H), 3.44 (d, J=3.2 Hz, 1H), 3.04 (d, J=10 Hz, 1H), 2.68~2.58 (m, 3H), 2.55 (d, J=10 Hz, 1H), 2.40~2.37 (m, 2H), 2.20~2.13 (m, 1H), 2.00~1.90 (m, 1H), 1.60 (m, 1H), 1.18 (s, 3H), 1.16~1.13 (m, 1H), 0.90 (d, J=7.2 Hz, 3H), 0.83 (d, J=7.2 Hz, 3H). ¹³C NMR (100 MHz, CDCl₃): δ 167.3, 163.3, 150.0, 143.2, 136.4, 136.1, 135.1, 131.6, 131.5, 131.3, 130.9, 130.4, 128.3, 126.3, 125.6, 73.0, 65.8, 65.5, 60.1, 60.1, 56.2, 54.0, 40.9, 36.8, 29.1, 28.0, 24.7, 17.7, 17.5, 16.7, 14.9. MS calcd for C₃₆H₃₀O₈F₆ (M+): 705.2, found 705.2.

3.2 Synthesis of Compound CK21S-003-b

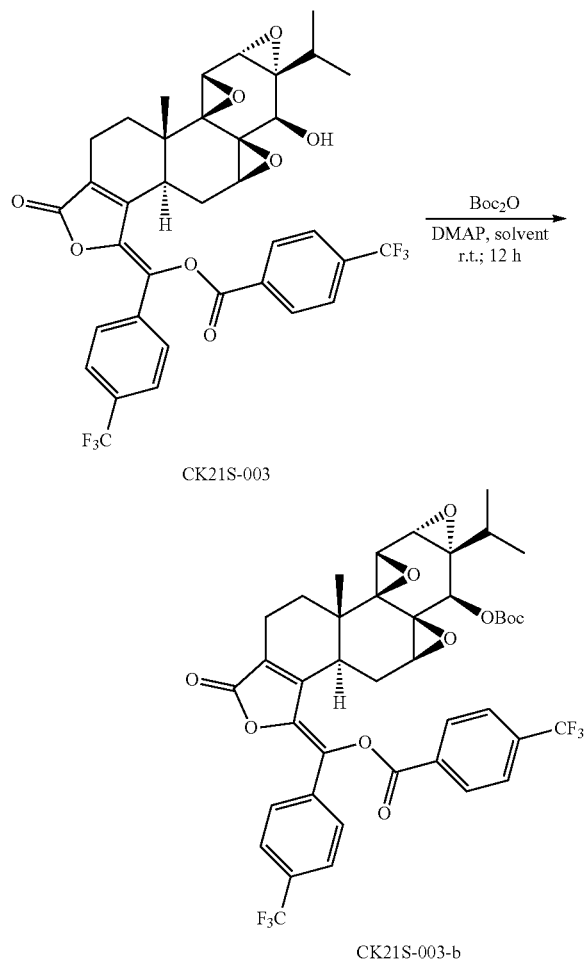

CK21S-003-b was prepared by using a similar method for preparation of CK21S-001-b, with a yield of 92% and a purity of more than 98%.

$^1$H NMR (400 MHz, CDCl$_3$): δ 8.37 (d, J=8.0 Hz, 2H), 7.89 (d, J=8.4 Hz, 2H), 7.81 (d, J=8.0 Hz, 2H), 7.67 (d, J=8.4 Hz, 2H), 4.36 (s, 1H), 3.73 (d. J=2.8 Hz, 1H), 3.44 (d, J=2.8 Hz, 1H), 2.72 (d, J=6.0 Hz, 1H), 2.63~2.57 (m, 2H), 2.38~2.36 (m, 2H), 1.96~1.84 (m, 2H), 1.62~1.59 (m, 1H), 1.46 (s, 9H), 1.19~1.16 (m, 1H), 1.14 (s, 3H), 0.86 (d, J=6.8 Hz, 3H), 0.80 (d, J=7.2 Hz, 3H). MS calcd for C$_{41}$H$_{38}$O$_{10}$F$_6$ (M+): 805.2, found 805.2.

Example 4: Preparation of Compound CK21S-004

4.1 Synthesis of Compound CK21S-004

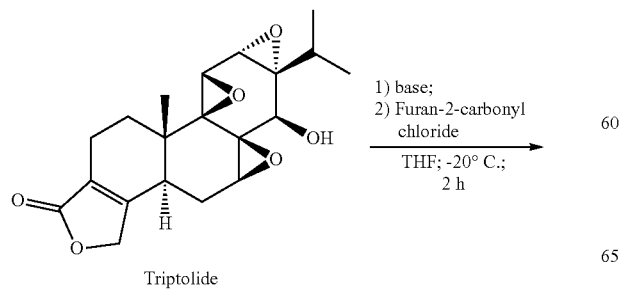

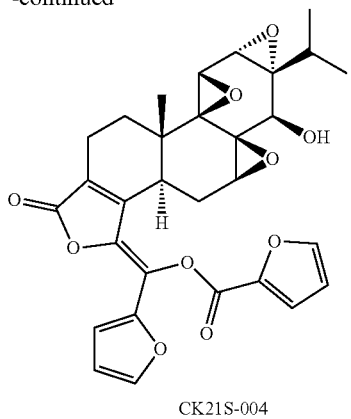

CK21S-004 was prepared by using a similar method for preparation of CK21S-001, with a yield of 88% and a purity of greater than 99%. The difference was that furan-2-carbonyl chloride was used in place of benzoyl chloride in example 1, and the other conditions were the same.

$^1$H NMR (400 MHz, CDCl$_3$): δ 7.74~7.72 (m, 1H), 7.54 (dd, 1H), 7.49 (d, 1H), 7.17 (d, 1H), 6.63 (q, 1H), 6.56 (q, 1H), 3.77 (d. J=3.2 Hz, 1H), 3.38 (d, J=2.4 Hz, 1H), 3.18 (d, J=10 Hz, 1H), 3.01 (d, J=3.2 Hz, 1H), 3.04~2.97 (m, 1H), 3.62 (d, J=10 Hz, 1H), 2.54~2.50 (m, 1H), 2.40~2.32 (m, 1H), 2.23~2.16 (m, 1H), 1.96~1.87 (m, 1H), 1.57~1.50 (m, 2H), 1.17 (s, 3H), 1.13~1.10 (m, 1H), 0.95 (d, J=7.2 Hz, 3H), 0.823 (d, J=7.2 Hz, 3H); $^{13}$C NMR (100 MHz, CDCl$_3$): δ 167.4, 155.6, 150.0, 148.0, 145.1, 144.2, 142.6, 140.3, 128.7, 124.6, 121.6, 115.5, 113.0, 112.6, 73.2, 66.1, 65.4, 60.6, 60.2, 56.3, 54.0, 40.4, 36.7, 29.1, 28.0, 24.4, 17.8, 17.7, 16.8, 14.8. MS calcd for C$_{30}$H$_{28}$O$_{10}$ (M+): 549.18, found 549.17.

4.2 Synthesis of Compound CK21S-004-b

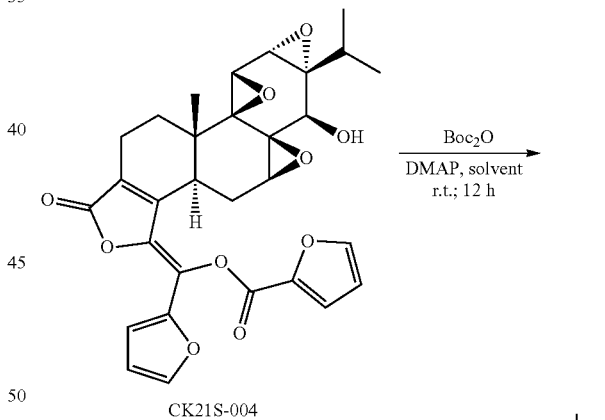

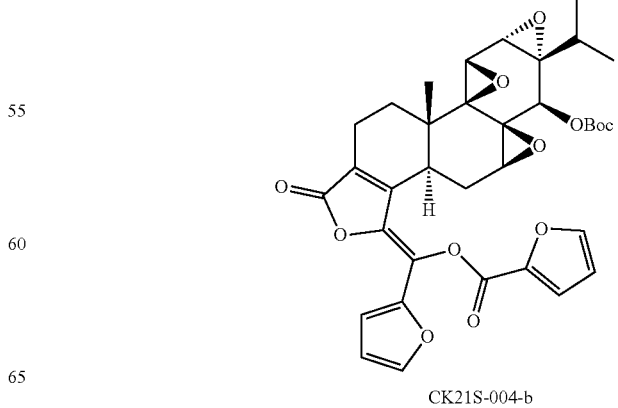

CK21S-004-b was prepared by using a similar method for preparation of CK21S-001-b, with a yield of 93% and a purity of greater than 99%.

¹H NMR (400 MHz, CDCl₃): δ 7.76 (d, J=0.8 Hz, 1H), 7.55 (d, J=3.2 Hz, 1H), 7.50 (d, J=1.2 Hz, 1H), 7.17 (d, J=3.2 Hz, 1H), 6.66 (dd, J=1.6 Hz, 3.6 Hz, 1H), 6.56 (dd, J=1.6 Hz, 3.6 Hz, 1H), 4.54 (s, 1H), 3.68 (d, J=3.2 Hz, 1H), 3.40 (d, J=2.8 Hz, 1H), 3.08 (d, J=6.4 Hz, 1H), 3.03~2.97 (m, 1H), 2.50~2.47 (m, 1H), 2.35~2.31 (m, 2H), 1.93~1.85 (m, 2H), 1.49 (s, 9H), 1.25 (m, 1H), 1.13 (s, 3H), 1.08~1.05 (m, 1H), 0.93 (d, J=6.8 Hz, 3H), 0.80 (d, J=6.8 Hz, 3H). MS calcd for C₃₅H₃₆O₁₂ (M+): 649.2, found 649.2.

Example 5: Preparation of Compound CK21S-005

5.1 Synthesis of Compound CK21S-005

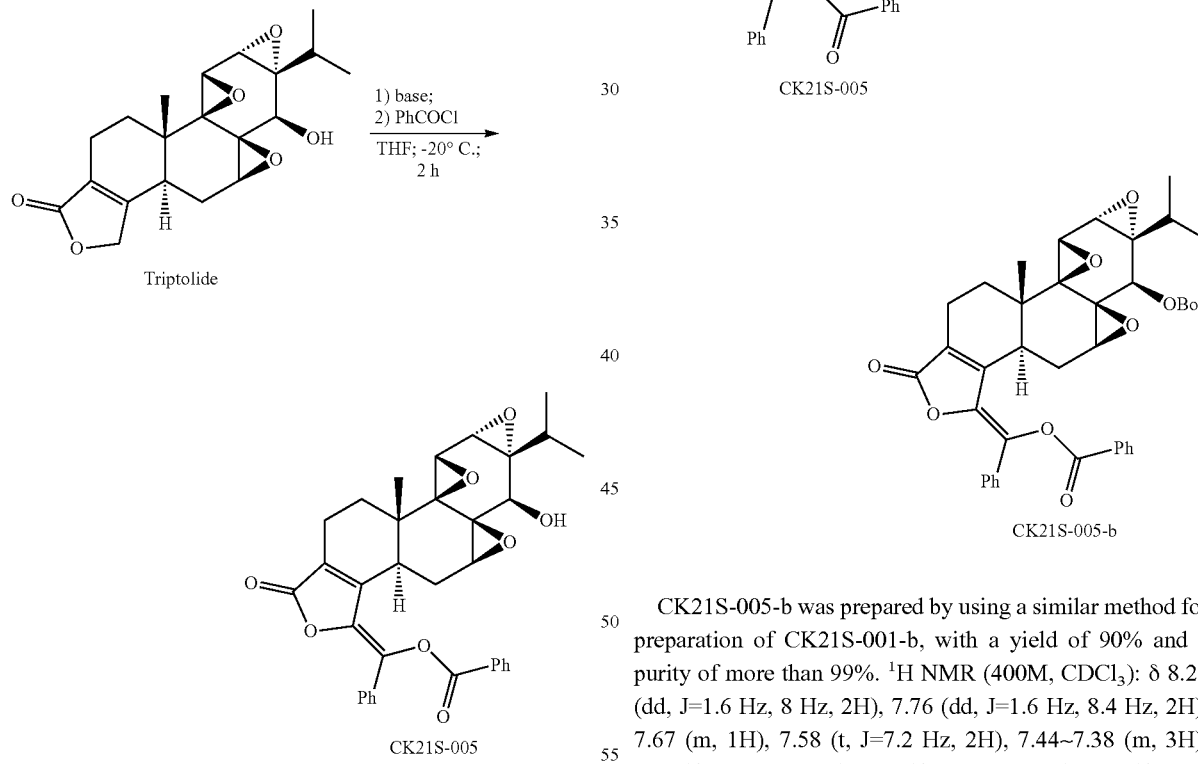

CK21S-005 was prepared by using a similar method for preparation of CK21S-001, with a yield of 80% and a purity of more than 99%. The reaction conditions are the same. ¹H NMR (400M, CDCl₃): δ 8.25 (dd, J=1.6 Hz, 8 Hz, 2H), 7.76 (dd. J=1.6 Hz, 8.4 Hz, 2H), 7.67 (m, 1H), 7.58 (t, J=7.2 Hz, 2H), 7.43~7.38 (m, 3H), 3.80 (d, J=3.2 Hz, 1H), 3.39 (d, J=2.8 Hz, 1H), 2.98 (d, J=10 Hz, 1H), 2.75~2.69 (m, 1H), 2.63~2.58 (m, 1H), 2.56 (d, J=6.4 Hz, 1H), 2.53 (d, J=10 Hz, 1H), 2.40~2.32 (m, 2H), 2.21~2.14 (m, 1H), 1.88 (dd, J=14.0 Hz, 13.2 Hz, 1H), 1.55~1.52 (m, 1H), 1.18~1.11 (m, 1H), 1.15 (s, 3H), 0.92 (d, J=7.2 Hz, 3H), 0.82 (d, J=6.8 Hz, 3H); ¹³C NMR (100 MHz, CDCl₃): δ 168.1, 164.5, 150.3, 142.2, 134.4, 133.5, 131.9, 130.5, 129.9, 129.2, 128.9, 128.6, 128.1, 128.0, 72.8, 65.8, 65.3, 60.7, 60.0, 56.5, 53.7, 40.7, 36.7, 29.3, 27.9, 24.6, 17.8, 17.6, 16.7, 15.0. MS calcd for C₃₄H₃₂O₈ (M+): 569.2, found 569.2.

5.2 Synthesis of Compound CK21S-005-b

CK21S-005-b was prepared by using a similar method for preparation of CK21S-001-b, with a yield of 90% and a purity of more than 99%. ¹H NMR (400M, CDCl₃): δ 8.26 (dd, J=1.6 Hz, 8 Hz, 2H), 7.76 (dd, J=1.6 Hz, 8.4 Hz, 2H), 7.67 (m, 1H), 7.58 (t, J=7.2 Hz, 2H), 7.44~7.38 (m, 3H), 4.30 (d, J=3.2 Hz, 1H), 3.70 (d, J=2.8 Hz, 1H), 3.40 (d, J=10 Hz, 1H), 2.75~2.68 (m, 1H), 2.62 (d, J=8.0 Hz, 1H), 2.58~2.54 (m, 1H), 2.33~2.27 (m, 2H), 1.91~1.81 (m, 2H), 1.49 (s, 9H), 1.11 (s, 3H), 0.92 (d, J=7.2 Hz, 3H), 0.82 (d, J=6.8 Hz, 3H); ¹³C-NMR (100 MHz, CDCl₃): δ 168.1, 164.5, 150.3, 142.2, 134.4, 133.5, 131.9, 130.5, 129.9, 129.2, 128.9, 128.6, 128.1, 128.0, 82.9, 73.9, 63.4, 63.1, 61.6, 58.6, 55.2, 54.5, 40.8, 36.7, 29.3, 27.9, 24.6, 17.8, 17.7, 16.7, 15.5. MS calcd for C₃₉H₄₀O₁₀ (M+): 669.2, found 669.2.

Example 6: Preparation of Compound CK21S-006

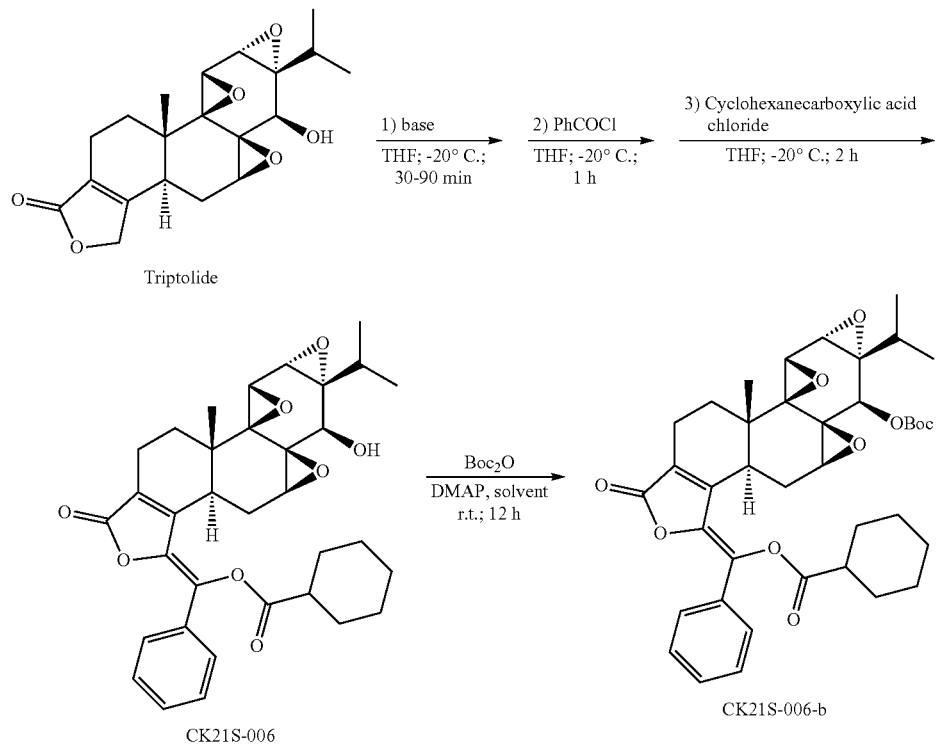

CK21S-006 was prepared by using a similar method for preparation of CK21S-001, with a yield of 75% and a purity of greater than 95%. The difference is that cyclohexylformyl chloride is used in place of furoyl chloride in example 1, and the other conditions are the same.

$^1$H NMR (400 MHz, CDCl$_3$): δ 7.67 (d, J=2.0 Hz, 1H), 7.65 (d, J=1.6 Hz, 1H), 7.43~7.35 (m, 2H), 3.86 (d, J=2.8 Hz, 1H), 3.50 (d, J=2.8 Hz, 1H), 3.42 (d, J=10.4 Hz, 1H), 3.37 (d, J=6.4 Hz, 1H), 3.0 (t, J=4.8 Hz, 1H), 2.71 (d, J=10.4 Hz, 1H), 2.62~2.55 (m, 2H), 2.37~2.32 (m, 2H), 2.28 (q, J=6.8 Hz, 1H), 2.22~2.16 (m, 2H), 1.97 (dd, J$_1$=13.2 Hz, J$_2$=2.0 Hz, 1H), 1.90~1.84 (m, 2H), 1.73 (d, J=11.6 Hz, 1H), 1.63~1.53 (m, 2H), 1.39~1.24 (m, 4H), 1.20 (s, 3H), 1.17~1.12 (m, 1H), 1.01 (d, J=7.2 Hz, 3H), 0.87 (d, J=7.2 Hz, 3H). MS calcd for C$_{34}$H$_{38}$O$_8$ (M+): 575.2, found 575.2.

CK21S-006-b was prepared by using a similar method for preparation of CK21S-001-b.

Example 7: Preparation of Compound CK21S-007

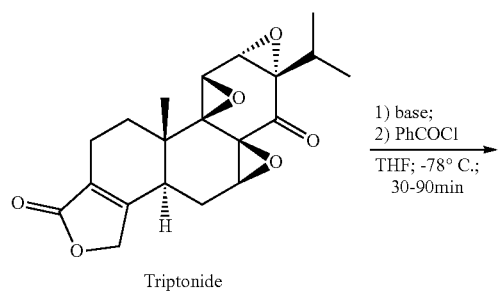

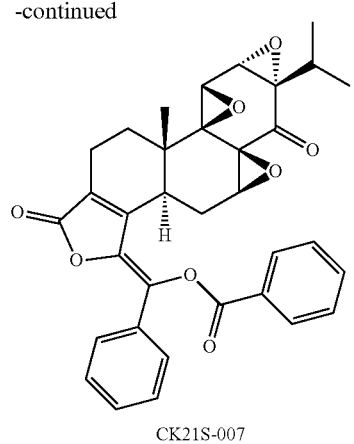

CK21S-007 was prepared from triptonide by using a similar method for preparation of CK21S-001, with a yield of 91% and a purity of more than 98%.

$^1$H NMR (400 MHz, CDCl$_3$): δ 8.22~8.25 (m, 2H), 7.77~7.79 (m, 2H), 7.59~7.63 (m, 1H), 7.49~7.54 (m, 2H), 7.37~7.41 (m, 3H), 3.94 (d, J=2.8 Hz, 1H), 3.71 (d, J=2.8 Hz, 1H), 2.79~2.85 (m, 1H), 2.56~2.61 (m, 2H), 2.33~2.45 (m, 2H), 2.20~2.29 (m, 1H), 1.88 (dd, J$_1$=13.6 Hz, J$_2$=14.8 Hz, 1H), 1.54~1.58 (m, 1H), 1.19~1.28 (m, 1H), 1.09 (s, 3H), 0.93 (d, J=6.8 Hz, 3H), 0.87 (d, J=6.8 Hz, 3H). MS calcd for C$_{34}$H$_{30}$O$_8$ (M+): 567.2. found 567.2.

Example 8: Preparation of Compound CK21S-008

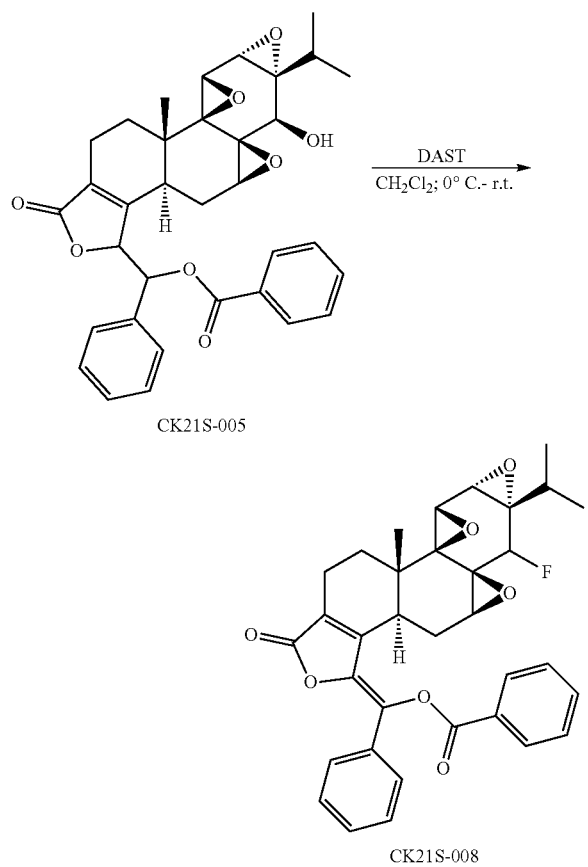

Compound CK21S-005 (57 mg, 0.1 mmol) was loaded into a dried three-necked round bottom flask, 3 mL of dichloromethane was added to dissolve and the mixture was cooled to 0° C. DAST F reagent (0.3 ml, 2.289 mmol) was taken and added dropwise into the reaction system, and the mixture was stirred thoroughly. The system slowly showed a yellowish color. After 4 hours of reaction, a saturated NaHCO$_3$ solution was added to quench the reaction. The mixture was diluted with ethyl acetate. The organic phase was washed with water (10 mL), saturated sodium carbonate (10 mL) and saturated sodium chloride (10 mL), dried over anhydrous sodium sulfate, filtered, and concentrated under reduced pressure. The crude product was separated and purified by silica gel chromatography (dichloromethane: ethyl acetate), and collected to obtain the target product CK21S-008 (white solid, 40 mg, yield 70%). $^1$H NMR (400M, CDCl$_3$) δ 0.89 (d, J=6.9 Hz, 3H), 1.18 (d, J=6.9 Hz, 3H), 1.13 (s, 3H), 1.23~1.28 (m, 1H), 1.51~1.54 (m, 1H), 1.83~1.90 (m, 1H), 1.92~1.99 (m, 1H), 2.25~2.36 (m, 2H), 2.58~2.61 (m, 1H), 2.74~2.80 (m, 1H), 2.98~2.99 (d, J=6.4 Hz, 1H), 3.34 (t, J=2.8 Hz, 1H), 3.70 (t, J=1.6 Hz, 1H), 4.95 (d, 1H), 7.38~7.45 (m, 3H), 7.47~7.49 (m, 1H), 7.56~7.60 (m, 2H), 7.67~7.70 (m, 1H), 7.75~7.78 (m, 2H), 8.23~8.25 (m, 1H); $^{19}$F NMR (400M, CDCl$_3$) δ 213.49. MS calcd for C$_{34}$H$_{31}$FO$_7$ (M+): 571.2, found 571.3.

Example 9: Preparation of Compound CK21S-005-b

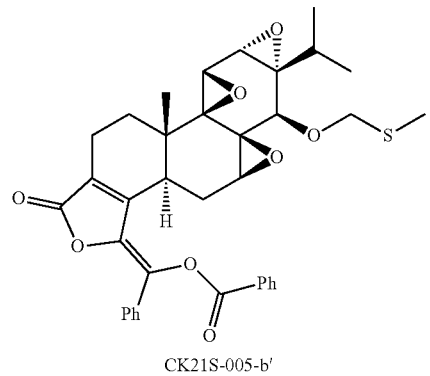 [SMILES: CSCO[C@@H]1[C@@]2(C(C)C)O[C@H]2[C@@H]2O[C@]23[C@]12O[C@H]2C[C@H]1C2=C(CC[C@@]13C)C(=O)O/C2=C(/OC(=O)c1ccccc1)c1ccccc1]

CK21S-005-b' was prepared from CK21S-005 by using a method similar to the preparation method in *J. Med. Chem.*, 2015, 58, 9334.

$^1$H NMR (400 MHz, CDCl$_3$): δ 8.25 (d, J=5.2 Hz, 2H), 7.74 (d, J=4.8 Hz, 2H), 7.68 (t, 1H), 7.61 (t, 2H), 7.43~7.38 (m, 3H), 4.94 (d, J=8 Hz, 1H), 4.85 (d, J=8 Hz, 1H), 3.69 (d, J=2 Hz, 1H), 3.38 (d, J=2 Hz, 1H), 3.21 (s, 1H), 2.62~2.72 (m, 2H), 2.44 (d, J=4 Hz, 1H), 2.35~2.33 (m, 2H), 2.29~2.24 (m, 1H), 2.13 (s, 3H), 1.86 (t, 1H), 1.59~1.57 (m, 1H), 1.16~1.09 (m, 1H), 1.13 (s, 3H), 0.90 (d, J=4.4 Hz, 3H), 0.78 (d, J=4.4 Hz, 3H). $^{13}$C NMR (100 MHz, CDCl$_3$): δ 168.1, 164.5, 150.5, 142.2, 134.4, 133.5, 132.0, 130.5, 129.8, 129.3, 129.0, 128.6, 128.1, 128.0, 75.6, 64.1, 63.8, 60.8, 58.4, 54.9, 53.8, 40.7, 36.8, 29.6, 29.0, 26.1, 24.4, 17.7, 17.3, 16.7, 15.0, 14.8. MS calcd for C$_{36}$H$_{36}$O$_{12}$S (M+): 628.2, found 628.2.

Example 10: Preparation of Compound CK21S-009

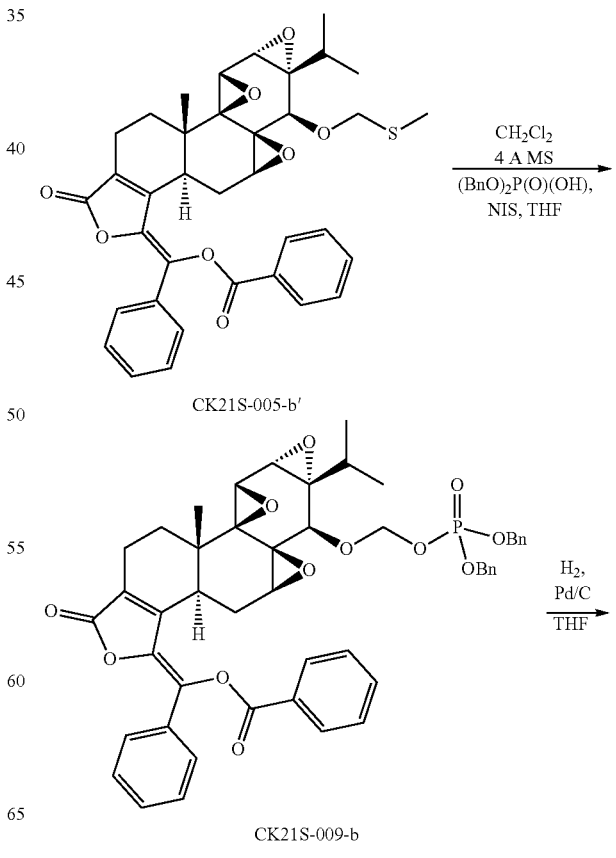

-continued

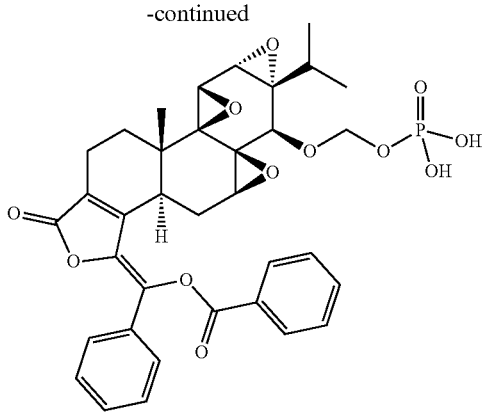

CK21S-009

Compound CK21S-005-b' was further derived to obtain Compound CK21S-009-b, and then Compound CK21S-009-b was deprotected to remove benzyl. The specific operation was as follows.

At room temperature, CK21S-005-b' (300 mg, 0.48 mmol) was dissolved in dichloromethane (10 mL), and a molecular sieve (300 mg) was added. The nitrogen was replaced and the mixture was stirred at 15-20° C. In addition, NIS (iodosuccinimide) (129 mg, 0.57 mmol) and dibenzyl phosphate (159 mg, 0.57 mmol) were dissolved in tetrahydrofuran (10 mL), and then slowly added dropwise into the reaction solution. After the dropwise addition was completed, the reaction was carried out at the room temperature for 3 hours. After the reaction was completed, the reaction solution was filtered, and then dichloromethane (120 mL) was added for dilution. Then, 0.1 M sodium thiosulfate (10 mL) was added for decolorization, and then the mixture was washed with a saturated sodium carbonate aqueous solution and a saturated sodium chloride aqueous solution. The organic phase was dried, and concentrated to obtain 300 mg of the product CK21S-009-b, which was directly subjected to the next reaction without column purification.

The palladium-carbon catalyst (160 mg) was placed in tetrahydrofuran (12 mL), then the mixture was cooled to 0° C. and stirred. CK21S-009-b (300 mg) was dissolved in THF (12 mL), and then slowly added into the above reaction solution. After the addition was completed, the hydrogen was replaced, and the reaction was maintained in a hydrogen atmosphere using a hydrogen balloon, and the reaction was performed at room temperature for 2 h. After the reaction was completed, the reaction solution was filtered, and then a small amount of sodium carbonate aqueous solution (50 mg $Na_2CO_3$, 4 mL) was added to adjust the pH to about 8-9. A small amount of water and methanol were added and the mixture was lyophilized and purified by the preparative liquid chromatography to obtain the target product (white solid, 80 mg, purity >99%). $^1$H NMR (400 MHz, CDCl$_3$) 8.20 (d, J=7.6 Hz, 2H), 7.76~7.79 (m, 1H), 7.65~7.71 (m, 4H), 7.42~7.51 (m, 3H), 7.27 (s, 2H), 4.89~4.97 (m, 2H), 3.75 (d, J=2.8 Hz, 1H), 3.38 (d, J=2.8 Hz, 1H), 3.32 (s, 1H), 2.73~2.82 (m, 2H), 2.31~2.40 (m, 2H), 2.22~2.26 (m, 2H), 1.81 (t, J=14 Hz, 1H), 1.23~1.30 (m, 1H), 1.10~1.11 (m, 1H), 0.97 (s, 3H), 0.82 (d, J=6.4 Hz, 3H), 0.65 (d, J=6.8 Hz, 3H). $^{13}$C NMR (100 MHz, CDCl$_3$): δ 167.2, 164.3, 150.3, 141.9, 135.0, 131.9, 131.7, 130.0, 129.8, 129.4, 128.9, 128.7, 127.6, 126.9, 90.7, 75.7, 63.7, 62.9, 60.5, 59.8, 54.7, 53.3, 36.1, 28.6, 25.3, 23.8, 17.3, 17.2, 16.8, 15.0. $^{31}$P-NMR (400 MHz, CDCl$_3$): δ −2.1. MS calcd for $C_{35}H_{35}O_2P$ (M$^-$): 677.2, found 627.2.

Example 11: Detection of In Vitro Antitumor Activity of Small Molecule Compounds CK21S-001, CK21S-001-b, CK21S-002, CK21S-002-b, CK21S-003, CK21S-003-b, CK21S-004, CK21S-004-b, CK21S-005, CK21S-005-b, CK21S-006, CK21S-006-b, CK21S-007, CK21S-008, CK21S-009 and Triptolide Tumor cells included AsPC-1 (human pancreatic cancer cell), PC-3 (human prostate cancer cell), and SK-OV-3 (human ovarian cancer cell). The source and culture medium of the cells were shown in Table 1 below.

TABLE 1

Tumor cell information

| Cell line | Supplier | Cat# | Tumor cell type | Medium |
|---|---|---|---|---|
| AsPC-1 | ATCC | CRT-1682 | human pancreatic cancer cell | RPMI 1640 + 10% FBS + 1X PS |
| PC-3 | ATCC | CRL-1435 | human prostate cancer cell | F-12K + 10% FBS + 1X PS |
| SK-OV-3 | ECACC | 91091004 | human ovarian cancer cell | McCoy's 5a + 10% FBS + 1X PS |

Triptolide was used as a positive control; the working concentrations of the test drug were 1 μM, 0.33 μM, 0.11 μM, 0.037 M, 0.012 μM, 0.004 μM, 1.4 nM, and 0.46 nM. After the tumor cells were revived, they were resuspended in the corresponding complete medium, placed in 5% $CO_2$, and cultured at 37° C. The tumor cells at the logarithmic growth stage were suspended in the corresponding complete medium to adjust the cell concentration. 90 μL of cell suspension was added into each well. The number of each type of cells was shown in Table 2 below. The cells were incubated at 37° C. in 5% $CO_2$ overnight. Each concentration of the test drug was added and the cells were further cultured for 48 hours. Finally. Promega CellTiter-Glo Luminescent Cell Viability Assay Kit was used for detection.

TABLE 2

Cell plating density

| Cell line | Cell number/well (96 well plate) |
|---|---|
| AsPC-1 | 5000 |
| PC-3 | 5000 |
| SK-OV-3 | 3000 |

The IC$_{50}$ values for in vitro antitumor activity of Compounds CK21S-000, CK21S-001-b, CK21S-002, CK21-002-b, CK21S-003, CK2S-003-b, CK2S-004, CK21S-004-b, CK21S-005, CK21S-005-b, CK21S-006, CK21S-006-b, CK2S-007, CK21S-008, CK2S-009 and triptolide were shown in Table 3. All compounds had in vitro antitumor activity, which was not much different from that of the positive control triptolide.

TABLE 3

In vitro antitumor activity as IC$_{50}$ (μM)

| Relative IC$_{50}$ (μM) | AsPC-1 | PC-3 | SK-OV-3 |
|---|---|---|---|
| CK21S-001 | 0.028 | 0.022 | 0.042 |
| CK21S-001-b | 0.030 | 0.029 | 0.048 |
| CK21S-002 | 0.071 | 0.056 | 0.070 |

TABLE 3-continued

In vitro antitumor activity as IC$_{50}$ (μM)

| Relative IC$_{50}$ (μM) | AsPC-1 | PC-3 | SK-OV-3 |
|---|---|---|---|
| CK21S-002-b | 0.042 | 0.042 | 0.057 |
| CK21S-003 | 0.014 | 0.018 | 0.028 |
| CK21S-003-b | 0.020 | 0.021 | 0.029 |
| CK21S-004 | 0.038 | 0.023 | 0.118 |
| CK21S-004-b | 0.096 | 0.045 | 0.129 |
| CK21S-005 | 0.040 | 0.030 | 0.041 |
| CK21S-005-b | 0.042 | 0.035 | 0.040 |
| CK21S-006 | 0.035 | 0.031 | 0.041 |
| CK21S-006-b | 0.036 | 0.034 | 0.045 |
| CK21S-007 | 0.049 | 0.043 | 0.050 |
| CK21S-008 | 0.035 | 0.030 | 0.038 |
| CK21S-009 | 0.030 | 0.027 | 0.032 |
| Triptolide | 0.014 | 0.014 | 0.016 |

Example 12

Detection of In Vitro Immunosuppressive Activity of Small Molecule Compounds CK21S-001, CK21S-001-b, CK21S-002, CK21S-002-b, CK21S-003, CK21S-003-b, CK21S-004, CK21S-004-b, CK21S-005, CK21S-005-b, CK21S-006, CK21S-006-b, CK21S-007, CK21S-008, CK21S-009 and Triptolide Preparation of Mouse Spleen Lymphocyte BALB/c mice were sacrificed by spinal dislocation, and their spleen was aseptically taken out. A single cell suspension was prepared and adjusted to the required concentration.

Cell Proliferation Test

A suspension of 4×10$^6$ cells/ml spleen lymphocytes was routinely prepared and 100 μL of cells was added into each well of a 96-well plate. 50 μL test sample in different concentrations was added and ConA (final concentration 5 μg/mL) was added to induce T lymphocyte activation and proliferation, or LPS (final concentration 10 μg/mL) (50 μL) was added to induce B lymphocyte activation and proliferation. The corresponding positive control and non-stimulating background control were set. The cells were cultured in 37° C., 5% CO$_2$ incubator for 48 h. 0.25 μCi $^3$H-thymidine was introduced and the cultivation was completed after 8 h. At the end of the cultivation, the culture plate was frozen at –20° C. in a freezer until measurement. The cells were collected on a glass fiber membrane with a cell harvester and then scintillation solution was added. The amount of $^3$H-thymine nucleotides incorporated into the cells' DNA was read on a Beta counter. The cell proliferation was represented by the cpm value.

IC$_{50}$ values for in vitro immunosuppressive activity of Compounds CK2S-001, CK21S-001-b, CK21S-002, CK21S-002-b, CK2S-003, CK21S-003-b, CK2S-004, CK21S-004-b, CK21S-005 CK21S-005-b and triptolide were shown in Table 4. All compounds had in vitro immunosuppressive activity, which was comparable to that of the positive control Triptolide.

TABLE 4

In vitro immunosuppressive activity as IC$_{50}$ (μM)

| IC$_{50}$ (μM) | mouse B lymphocytes induced by LPS | mouse T lymphocytes induced by ConA |
|---|---|---|
| CK21S-001 | 0.006 | 0.008 |
| CK21S-001-b | 0.010 | 0.011 |
| CK21S-002 | 0.020 | 0.021 |
| CK21S-002-b | 0.010 | 0.012 |
| CK21S-003 | 0.004 | 0.006 |
| CK21S-003-b | 0.005 | 0.006 |
| CK21S-004 | 0.009 | 0.012 |
| CK21S-004-b | 0.025 | 0.030 |
| CK21S-005 | 0.010 | 0.012 |
| CK21S-005-b | 0.009 | 0.011 |
| CK21S-006 | 0.008 | 0.010 |
| CK21S-006-b | 0.015 | 0.016 |
| CK21S-007 | 0.017 | 0.015 |
| CK21S-008 | 0.009 | 0.010 |
| CK21S-009 | 0.008 | 0.008 |
| Triptolide | 0.004 | 0.005 |

Example 13

Detection of In Vivo Antitumor Activity of Small Molecule Compound CK21S-005 and Triptolide Human pancreatic cancer cell AsPC-1 was subcutaneously inoculated on the right abdominal side of male nude mice. Tumor-bearing mice were randomly divided into 5 groups: negative control group (Control, n=8, blank emulsion, i.p./i.v., qd); Triptolide group (Triptolide, n=8, 0.25 mg/kg, i.v., qd); positive control group (Gemcitabine, n=8, 50 mg/kg, i.p., tiw); CK21S-005 emulsion group (CK21S-005 emulsion, n=8, 5 mg/kg, i.p./i.v., qd); and CK21S-005 emulsion group (CK21S-005 emulsion, n=8, 2.5 mg/kg, i.p./i.v., qd). Mice were administered in groups until the end of the experiment. The changes in tumor size and tumor-bearing mouse weight over time were monitored during the 2-week administration period, and tumors were weighed at the end of the experiment to comprehensively evaluate the inhibitory effect of the drug CK21S-005 on tumor growth.

The preparation method of the emulsion was as follows. A prescribed amount of injection oil was weighed and heated to 70-90° C. A prescribed amount of raw material was weighed, dispersed in the oil phase and completely dissolved under shear-stirring to form an oil phase. A prescribed amount of injection water was weighed and heated to 70° C. A prescribed amount of phospholipid, co-emulsifier, glycerin, etc. were added and dispersed under shear to form an aqueous phase. Under high-speed shearing condition, the oil phase was slowly added into the aqueous phase and the mixture was sheared for 3-15 min to form a primary emulsion. The primary emulsion was homogenized under high pressure at 400-1000 bar for 3-6 times to form a uniformly distributed emulsion. The emulsion was subpacked in a glass container (such as ampule) and subjected to moist heat sterilization at 121° C. for 15 minutes. The sterilized sample was sent to QC laboratory for detection.

The tumor volume and tumor weight data (see FIG. 1) showed that the intravenous or intraperitoneal administration of CK21S-005 emulsion (5 mg/kg, labeled as 5 mpk), CK21S-005 emulsion (2.5 mg/kg, labeled as 2.5 mpk), or Triptolide emulsion (0.25 mg/kg) had significant inhibition effect on pancreatic cancer AsPC-1 tumor-bearing mice, which was significantly better than that of the positive control gemcitabine group.

Figure 2:
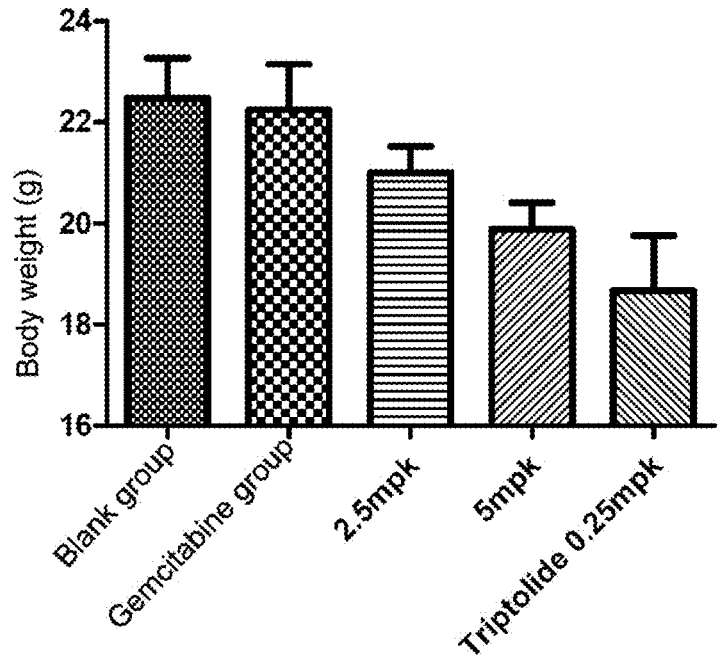
FIG. 2 is a graph of weight data.

The mouse weight data (see FIG. 2) showed that the administration of CK21S-005 emulsion (2.5 mg/kg. 5 mg/kg) or Triptolide emulsion (0.25 mg/kg) (intravenous or intraperitoneal administration) significantly reduced body weight of mouse. From the 6th day of continuous i.v. administration of Triptolide emulsion (0.25 mg/kg), the mice died one after another, with severe ulceration in the tail, and autopsy showed black lung necrosis in the whole lung, and ⅝ of the mice died. Triptolide emulsion was highly toxic at this dose which was a lethal dose. No death was observed in the CK21S-005 emulsion group, and all 8 mice survived to the end of the administration. It can be seen that the safety of CK21S-005 is better than that of triptolide.

All documents mentioned in the present invention are incorporated by reference in the present application, as if each document was individually incorporated by reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A compound represented by formula I, or a pharmaceutically acceptable salt thereof, or an enantiomer, a diastereomer, or a tautomer thereof,

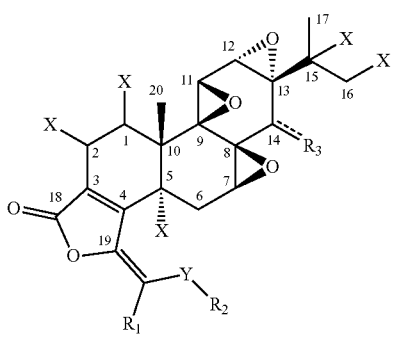

I wherein,
$R_1$ is a substituted or unsubstituted group selected from the group consisting of: C1-C6 alkyl, C3-C8 cycloalkyl, C2-C6 alkenyl, C3-C8 cycloalkenyl, C2-C6 alkynyl, C6-C10 aryl, C7-C15 arylalkyl and 4-8 membered heteroaryl;
Y is O, NH or S;
$R_2$ is a substituted or unsubstituted group selected from the group consisting of: C1-C6 alkyl, C3-C8 cycloalkyl, C2-C6 alkenyl, C3-C8 cycloalkenyl, C2-C6 alkynyl, C6-C10 aryl, C7-C15 arylalkyl, 4-8 membered heteroaryl and —C(=O)$R_4$, wherein $R_4$ is a substituted or unsubstituted group selected from the group consisting of: C1-C6 alkyl, C3-C8 cycloalkyl, C2-C6 alkenyl, C3-C8 cycloalkenyl, C2-C6 alkynyl, C6-C10 aryl, C7-C15 arylalkyl and 4-8 membered heteroaryl;
═══ represents a double bond or a single bond, when it is a double bond, $R_3$ is O; when it is a single bond, $R_3$ is $OR_5$, F or SH, and $R_5$ is H, Boc, TBS, TES, $CH_2SCH_3$, $CH_2OCH_3$, —$CH_2OP(=O)(OH)_2$, —$CH_2OP(=O)(OBn)_2$, —$OP(=O)(OH)_2$, —$OP(=O)(OBn)_2$, —COOH, monosaccharide, or folic acid;
each X is independently H, OH or halogen;
each of the above term "substituted" independently means that one or more hydrogen atoms on the group are substituted with a substituent selected from the group consisting of: halogen, —OH, $NH_2$, CN, COOH, —OP(=O)(OH)$_2$, unsubstituted or halogenated C1-C8 alkyl, unsubstituted or halogenated C3-C8 cycloalkyl, unsubstituted or halogenated C1-C8 alkoxy, unsubstituted or halogenated C2-C6 alkenyl, unsubstituted or halogenated C2-C6 alkynyl, unsubstituted or halogenated C2-C6 acyl, unsubstituted or halogenated C2-C6 amido, unsubstituted or halogenated 5-8 membered aryl, unsubstituted or halogenated 5-8 membered heteroaryl, unsubstituted or halogenated 4-8 membered saturated heterocycle or carbocycle; wherein each of the above heteroaryl groups independently contains 1-3 heteroatoms selected from the group consisting of N, O and S.

2. The compound of claim 1, wherein each X is H.

3. The compound of claim 1, wherein Y is O.

4. The compound of claim 1, wherein $R_1$ is a substituted or unsubstituted group selected from the group consisting of: C1-C4 alkyl, C3-C6 cycloalkyl, C6-C10 aryl or 4-8 membered heteroaryl, wherein the term "substituted" means one or more hydrogen atoms on the group are substituted with a substituent selected from the group consisting of halogen, —OH, unsubstituted or halogenated C1-C4 alkyl, and unsubstituted or halogenated C1-C3 alkoxy.

5. The compound of claim 1, wherein $R_2$ is a substituted or unsubstituted group selected from the group consisting of: C1-C4 alkyl, C7-C10 arylalkyl, 4-6 membered heteroaryl or —C(=O)$R_4$, wherein $R_4$ is a substituted or unsubstituted group selected from the group consisting of: C1-C4 alkyl, C3-C6 cycloalkyl, C6-C10 aryl, C7-C15 arylalkyl or 4-8 membered heteroaryl, wherein the term "substituted" means one or more hydrogen atoms on the group are substituted with a substituent selected from the group consisting of halogen, —OH, unsubstituted or halogenated C1-C4 alkyl, and unsubstituted or halogenated C1-C3 alkoxy.

6. The compound of claim 1, wherein the compound is:

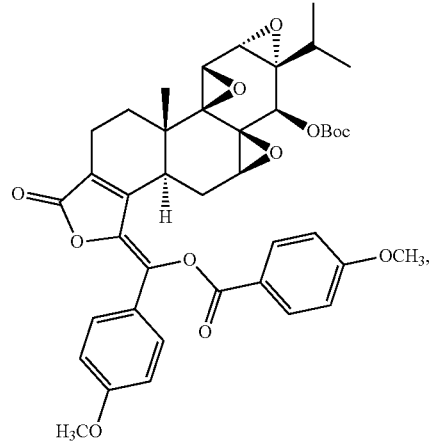

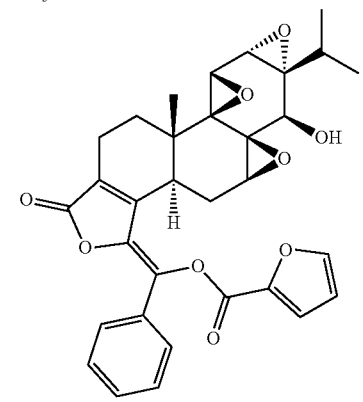

,

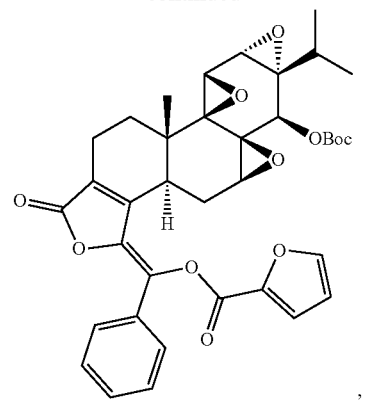
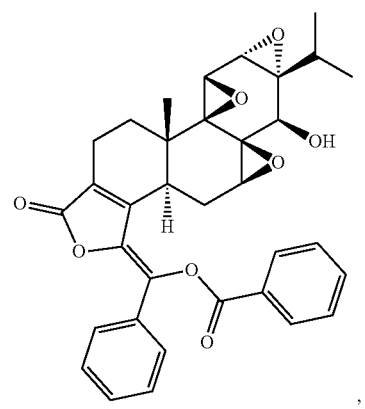
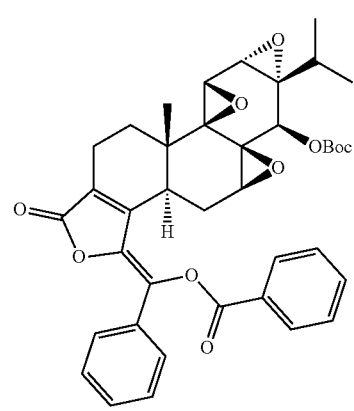
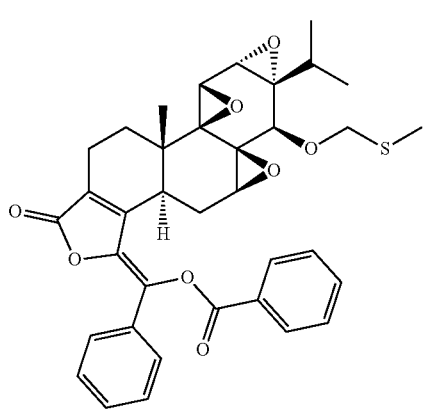
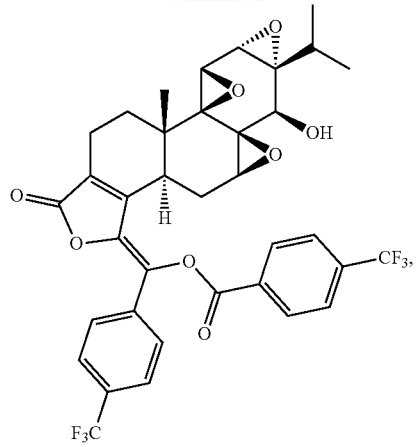
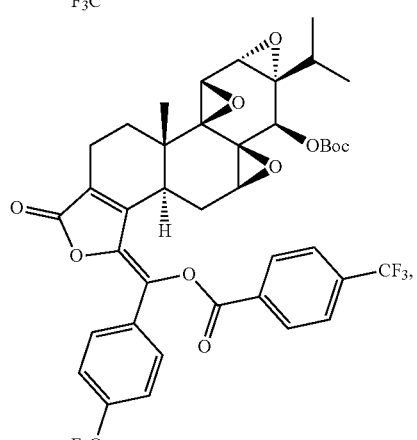
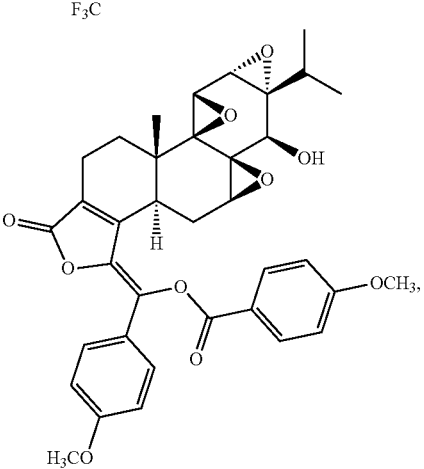
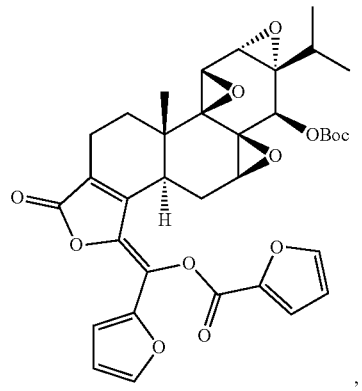

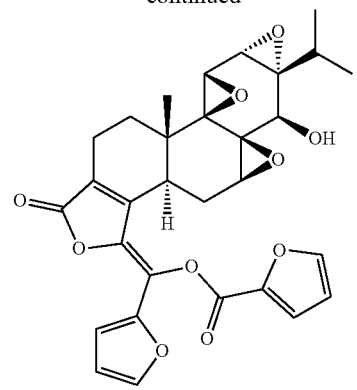

,

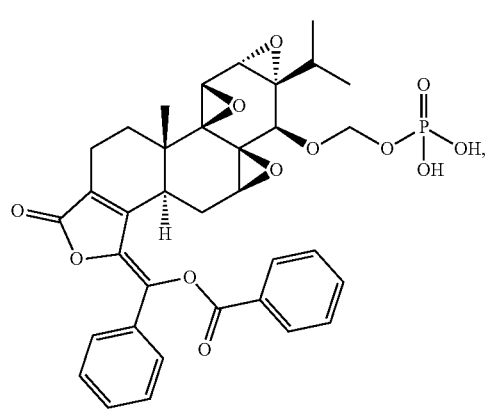

,

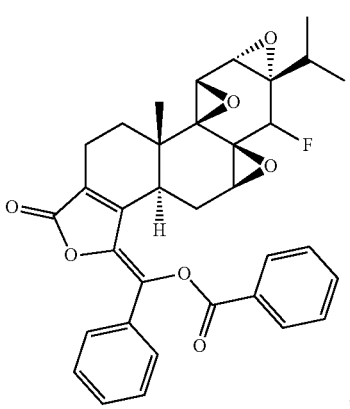

,

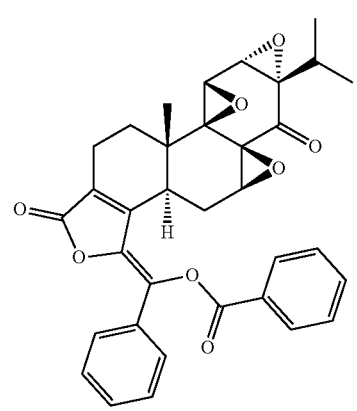

,

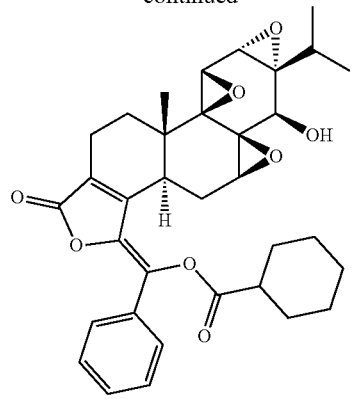

,

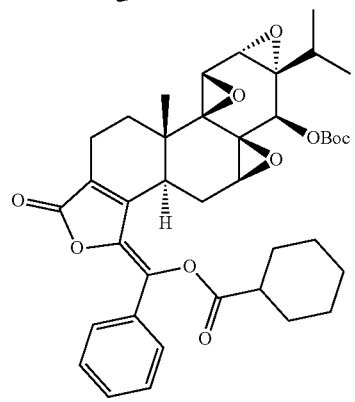

or

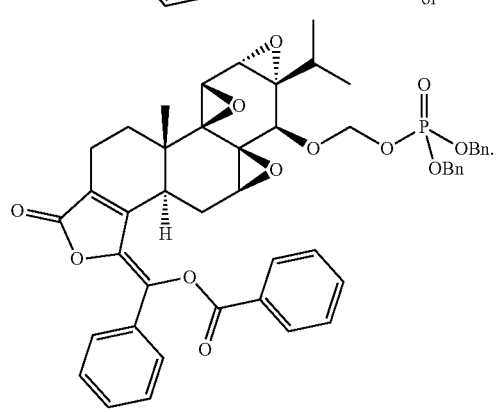

7. A method for preparing the compound of claim 1, wherein when $R_2$ is —C(=O)$R_4$ and $R_1$=$R_4$, the preparation method comprises the following steps:

reacting triptolide with an acylating agent, thereby obtaining a compound of formula II, and derivatizing the compound of formula II, thereby obtaining a compound of formula III, wherein the acylating agent is $R_1COCl$, $R_1COBr$ or $R_1COOCOR_1$;

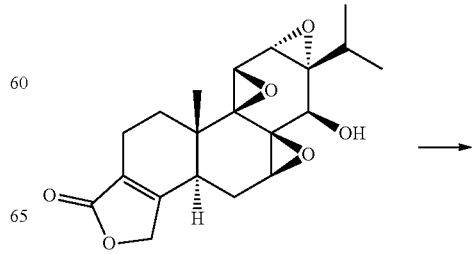

-continued

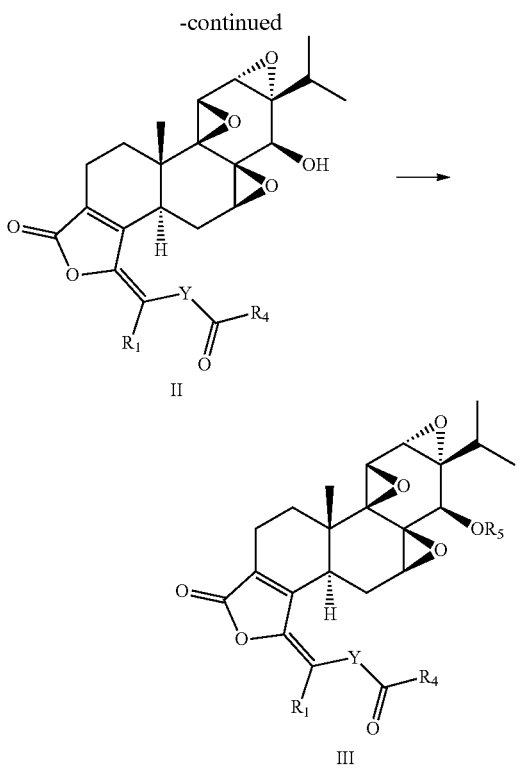

II

III or when R₂ is —C(=O)R₄ and R₁≠R₄, the preparation method comprises the following steps:

reacting triptolide with a first acylating reagent and a second acylating reagent respectively, thereby obtaining a compound of formula II, and deriving the compound of formula II, thereby obtaining a compound of formula III, wherein the first acylating agent is $R_1COCl$, $R_1COBr$ or $R_1COOCOR_1$, and the second acylating agent is $R_4COCl$, $R_4COBr$, or $R_4COOCOR_4$; wherein $R_1$, $R_4$, and $R_5$ are defined as in claim 1.

8. A pharmaceutical composition, comprising the compound of claim 1, or the pharmaceutically acceptable salt thereof, or the enantiomer, diastereomer, or tautomer thereof; and a pharmaceutically acceptable carrier.

9. A method for treating a cancer comprising administering the compound of claim 1, or the pharmaceutically acceptable salt thereof, or the enantiomer, diastereomer, or tautomer thereof to a subject in need thereof, wherein the cancer is selected from the group consisting of pancreatic cancer, prostate cancer, ovarian cancer, leukemia, and liver cancer.

10. A method for treating cancer comprising administering the compound of claim 1, or the pharmaceutically acceptable salt thereof, or the enantiomer, diastereomer, or tautomer thereof to a subject in need thereof, wherein the cancer is selected from the group consisting of pancreatic cancer, prostate cancer and ovarian cancer.

11. A method for treating cancer comprising administering the compound of claim 1, or the pharmaceutically acceptable salt thereof, or the enantiomer, diastereomer, or tautomer thereof to a subject in need thereof, wherein the cancer is pancreatic cancer.

* * * * *